United States Patent
Maurer et al.

(10) Patent No.: US 9,737,682 B2
(45) Date of Patent: Aug. 22, 2017

(54) HUMIDIFICATION OF RESPIRATORY GASES

(75) Inventors: Dimitri Marco Maurer, Umina (AU); Hargopal Verma, Parramatta (AU); Ian Malcolm Smith, Westleigh (AU); Richard Llewelyn Jones, Hornsby Heights (AU)

(73) Assignee: RESMED LIMITED, Bella Vista (AU)

( * ) Notice: Subject to any disclaimer, the term of this patent is extended or adjusted under 35 U.S.C. 154(b) by 1299 days.

(21) Appl. No.: 13/584,133

(22) Filed: Aug. 13, 2012

(65) Prior Publication Data

US 2013/0008440 A1    Jan. 10, 2013

Related U.S. Application Data

(60) Provisional application No. 61/522,763, filed on Aug. 12, 2011.

(51) Int. Cl.
*A61M 16/16* (2006.01)
*A61M 16/10* (2006.01)

(52) U.S. Cl.
CPC .......... *A61M 16/16* (2013.01); *A61M 16/109* (2014.02); *A61M 2205/3379* (2013.01); *A61M 2205/3382* (2013.01); *A61M 2205/3386* (2013.01); *A61M 2205/3389* (2013.01); *A61M 2205/502* (2013.01); *A61M 2205/584* (2013.01)

(58) Field of Classification Search
CPC . F24F 6/00–6/18; A61M 16/00; A61M 16/16; A61M 16/162; A61M 16/10; A61M 16/1045; A61M 2205/60; A61M 2205/584; A61M 2205/3389; A61M 16/1075–16/109; A61M 16/14; A61M 2205/502; A61M 2205/3379–2205/3386; B65D 5/4212; F16K 37/0058
USPC ................ 261/119.1, 135, DIG. 65; 141/95; 137/551, 558–558; 73/427; 206/459.1; 116/227
See application file for complete search history.

(56) References Cited

U.S. PATENT DOCUMENTS

| | | | | |
|---|---|---|---|---|
| 3,873,806 A | * | 3/1975 | Schossow | F24F 6/025 126/113 |
| 4,028,444 A | * | 6/1977 | Brown | A61M 16/16 128/200.13 |
| 5,025,618 A | * | 6/1991 | Braun | B60K 15/03177 56/16.7 |

(Continued)

FOREIGN PATENT DOCUMENTS

WO    WO 2010/031126 A1    3/2010

*Primary Examiner* — Justine Yu
*Assistant Examiner* — Tu Vo
(74) *Attorney, Agent, or Firm* — Nixon & Vanderhye, P.C.

(57) ABSTRACT

A tub is configured to contain a supply of water and be inserted into a chamber of a humidifier. The tub includes a tub base configured to contain a supply of water and a tub lid connected to the tub base. The tub lid includes an inlet configured to receive a flow of breathable gas to be humidified and an outlet for the humidified flow of breathable gas. The tub further includes a water level indicator configured to indicate a level of the supply of water in the tub base. The water level indicator includes an inclined portion configured to direct the flow of breathable gas from the inlet away from the outlet. The water level indicator may be visible through the inlet.

68 Claims, 25 Drawing Sheets

(56) References Cited

U.S. PATENT DOCUMENTS

| | | | |
|---|---|---|---|
| 6,398,197 B1* | 6/2002 | Dickinson | A61M 16/16 261/119.1 |
| 6,718,974 B1* | 4/2004 | Moberg | A61M 16/16 128/203.17 |
| 6,726,868 B1* | 4/2004 | Panfili | B29C 45/1671 264/247 |
| 7,909,032 B2* | 3/2011 | Feldhahn | A61M 16/00 128/203.16 |
| 2006/0272639 A1* | 12/2006 | Makinson | A61M 16/105 128/203.16 |
| 2007/0210462 A1* | 9/2007 | Felty | F24F 6/00 261/72.1 |
| 2008/0072900 A1* | 3/2008 | Kenyon | A61M 16/0051 128/204.18 |
| 2008/0302361 A1* | 12/2008 | Snow | A61M 16/1075 128/202.27 |
| 2009/0194106 A1* | 8/2009 | Smith | A61M 16/0816 128/203.16 |
| 2009/0223514 A1 | 9/2009 | Smith et al. | |
| 2010/0132708 A1* | 6/2010 | Martin | A61M 16/0066 128/204.17 |
| 2010/0147299 A1* | 6/2010 | Row | A61M 16/1075 128/203.27 |
| 2010/0154796 A1* | 6/2010 | Smith | A61M 16/16 128/203.26 |
| 2011/0017212 A1* | 1/2011 | Kenyon | A61M 16/00 128/203.26 |
| 2011/0155132 A1* | 6/2011 | Virr | A61M 16/0816 128/203.26 |
| 2011/0156288 A1* | 6/2011 | Ahn | F24F 6/12 261/30 |

* cited by examiner

HUMIDIFICATION OF RESPIRATORY GASES

CROSS REFERENCE TO RELATED APPLICATIONS

This application claims the benefit of U.S. Provisional Application No. 61/522,763 filed Aug. 12, 2011, incorporated herein by reference.

In addition, the entire contents of International Application PCT/AU2009/001232, filed Sep. 17, 2009 (and published as WO 2010/031126 A1), and U.S. application Ser. No. 12/847,021, filed Jul. 30, 2010, are incorporated herein by reference.

FIELD OF THE TECHNOLOGY

The present technology relates to systems and method to control the humidity of breathable gases used in all forms of respiratory apparatus ventilation systems including invasive and non-invasive ventilation. Continuous Positive Airway Pressure (CPAP), Bi-Level therapy and treatment for sleep disordered breathing (SDB) conditions such as Obstructive Sleep Apnea (OSA), and for various other respiratory disorders and diseases.

BACKGROUND OF THE TECHNOLOGY

Respiratory apparatuses commonly have the ability to alter the humidity of the breathable gas in order to reduce drying of the patient's airway and consequent patient discomfort and associated complications. The use of a humidifier placed between the flow generator and the patient mask produces humidified gas that minimizes drying of the nasal mucosa and increases patient airway comfort. In addition in cooler climates, warm air applied generally to the face area in and about the mask is more comfortable than cold air.

Many humidifier types are available, although the most convenient form is one that is either integrated with or configured to be coupled to the relevant respiratory apparatus. While passive humidifiers can provide some relief, generally a heated humidifier is required to provide sufficient humidity and temperature to the air so that the patient will be comfortable. Humidifiers typically comprise a water tub having a capacity of several hundred milliliters, a heating element for heating the water in the tub, a control to enable the level of humidification to be varied, a gas inlet to receive gas from the flow generator, and a gas outlet adapted to be connected to a patient conduit that delivers the humidified gas to the patient's mask.

Typically, the heating element is incorporated in a heater plate which sits under, and is in thermal contact with, the water tub.

SUMMARY OF THE TECHNOLOGY

One aspect of the technology is a humidifier for a respiratory apparatus that includes a chamber that is pressurisable to reduce the pressure on joints of the humidifier tub (which is placed within the pressurised chamber) to reduce leaks.

A further aspect of the technology is a humidifier for a respiratory apparatus that includes a chamber that is pressurisable to reduce tolerances for insertion of a tub with respect to seals on an inlet and an outlet tube of the humidifier chamber.

A still further aspect of the technology is a humidifier for a respiratory apparatus that directs air over the surface of a supply of water contained in a tub to humidify a flow of breathable gas regardless of the water level.

Another aspect of the technology is a humidifier for a respiratory apparatus that includes seals that are not under the supply of water, thus reducing a risk of water leakage.

Yet another aspect of the technology is a humidifier for a respiratory apparatus that includes a tub that is disposable.

Another aspect of the technology is a humidifier for a respiratory apparatus that includes a tub that is cleanable and/or reusable by disinfection and/or sterilisation methods.

Still another aspect of the technology is a humidifier for a respiratory apparatus that includes a tub that comprises a water level indicator, for example a water level indicator that indicates a maximum fill level, working, indicia and/or a marking, etc, e.g., arranged in a way (e.g., on an incline) that allows visual discrimination of water level.

A still further aspect of the technology relates to a water level indicator in a tub that may be viewed through a window of the humidifier. An even further aspect of the technology relates to a water level indicator that appears to change colour as the water level changes, for example appears to be a darker colour or mixture of colours, in order to enhance visual discrimination of the water level.

A further aspect of the technology relates to a tub that is removable from the humidifier and is configured to prevent any water flowing out of the tub from flowing back into the flow generator.

A still further aspect of the technology is a humidifier for a respiratory apparatus that prevents water from spilling back into a flow generator, or blower, that generates a flow of breathable gas.

According to an example, a tub configured to contain a supply of water and to be inserted into a chamber of a humidifier comprises a tub base configured to contain a supply of water; a tub lid connected to the tub base, the tub lid including an inlet configured to receive a flow of breathable gas to be humidified and an outlet for the humidified flow of breathable gas; and a water level indicator configured to indicate a level of the supply of water in the tub base, the water level indicator comprising an inclined portion configured to direct the flow of breathable gas from the inlet away from the outlet, and to improve the efficiency of moisture pick-up in to the air. This is achieved by the geometry of the inclined portion to promote swirl of the air above the water level.

According to another example, a tub configured to contain a supply of water and to be inserted into a chamber of a humidifier comprises a tub base configured to contain a supply of water; a tub lid connected to the tub base, the tub lid including an inlet configured to receive a flow of breathable gas to be humidified and an outlet for the humidified flow of breathable gas; and a water level indicator configured to indicate a level of the supply of water in the tub base. The water level indicator comprises an inclined portion, and the water level indicator is visible through the tub air inlet.

According to still another example, a humidifier for humidifying a flow of breathable gas to be delivered to a patient comprises a chamber configured to receive the flow of breathable gas; a lid provided on the chamber and being movable between an open position and a closed position; a seal provided on the lid, the seal being configured to seal the chamber such that the flow of breathable gas pressurizes the chamber; and a tub as disclosed herein.

According to a further example, a respiratory apparatus for providing a humidified flow of breathable gas to a patient comprises a flow generator to generate a flow of breathable gas and a humidifier and/or a tub as disclosed herein.

BRIEF DESCRIPTION OF THE DRAWINGS

Embodiments of the technology will now be described with reference to the accompanying drawings, in which.

DETAILED DESCRIPTION OF ILLUSTRATED EMBODIMENTS

PAP System

Figure 1:
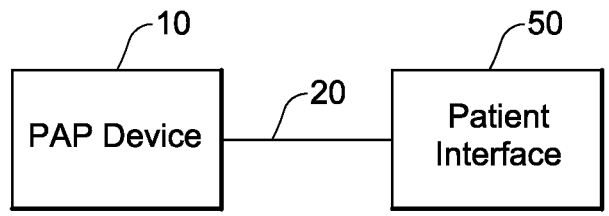
FIG. 1 schematically depicts a PAP system according to a sample embodiment.

As schematically shown in FIG. 1, a Positive Airway Pressure (PAP) system, for example a Continuous Positive Airway Pressure (CPAP) system, generally includes a PAP device 10, an air delivery conduit 20 (also referred to as a tube or tubing), and a patient interface 50. In use, the PAP device 10 generates a supply of pressurized air that is delivered to the patient via an air delivery conduit 20 that includes one end coupled to the outlet of the PAP device 10 and an opposite end coupled to the inlet of the patient interface 50. The patient interface comfortably engages the patient's face and provides a seal. The patient interface or mask may have any suitable configuration as is known in the art, e.g., full-face mask, nasal mask, oro-nasal mask, mouth mask, nasal prongs, etc. Also, headgear may be utilized to comfortably support the patient interface in a desired position on the patient's face.

Figure 2:
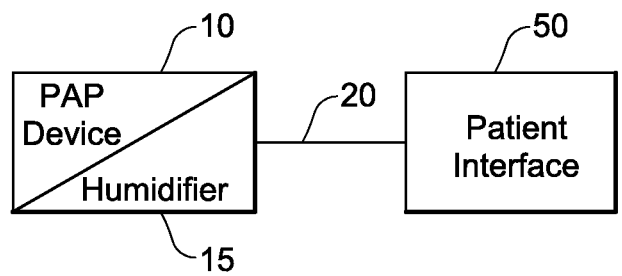
FIG. 2 schematically depicts a PAP system according to another sample embodiment.

In embodiments, a humidifier may be incorporated or integrated into the PAP device or otherwise provided downstream of the PAP device. In such embodiments, the air delivery conduit 20 may be provided between the patient interface 50 and the outlet of the humidifier 15 as schematically shown in FIG. 2.

Figure 3:
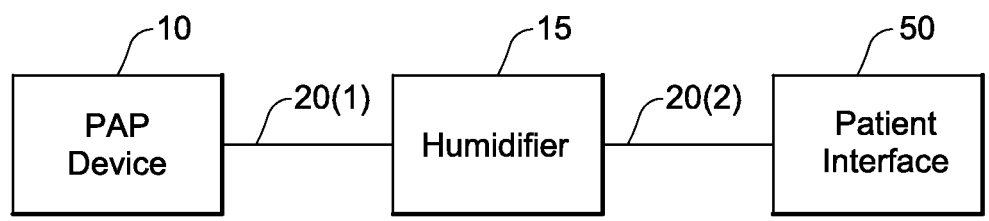
FIG. 3 schematically depicts a PAP system according to another sample embodiment.

It should be appreciated that the air delivery conduit may be provided along the air delivery path in other suitable manners. For example, as schematically shown in FIG. 3, the humidifier 15 may be a separate component from the PAP device 10 so that an air delivery conduit 20(1) is placed between the PAP device 10 and the humidifier 15 and another air delivery conduit 20(2) is placed between the humidifier 15 and the patient interface 50.

Generally, a heated humidifier is used to provide sufficient humidity and temperature to the air so that the patient will be comfortable. In such embodiment, the air delivery conduit may be heated to heat the gas and prevent "rain-out" or condensation forming on the inside of the conduit as the gas is supplied to the patient. In this arrangement, the air delivery conduit may include one or more wires or sensors associated with heating.

Figure 4:
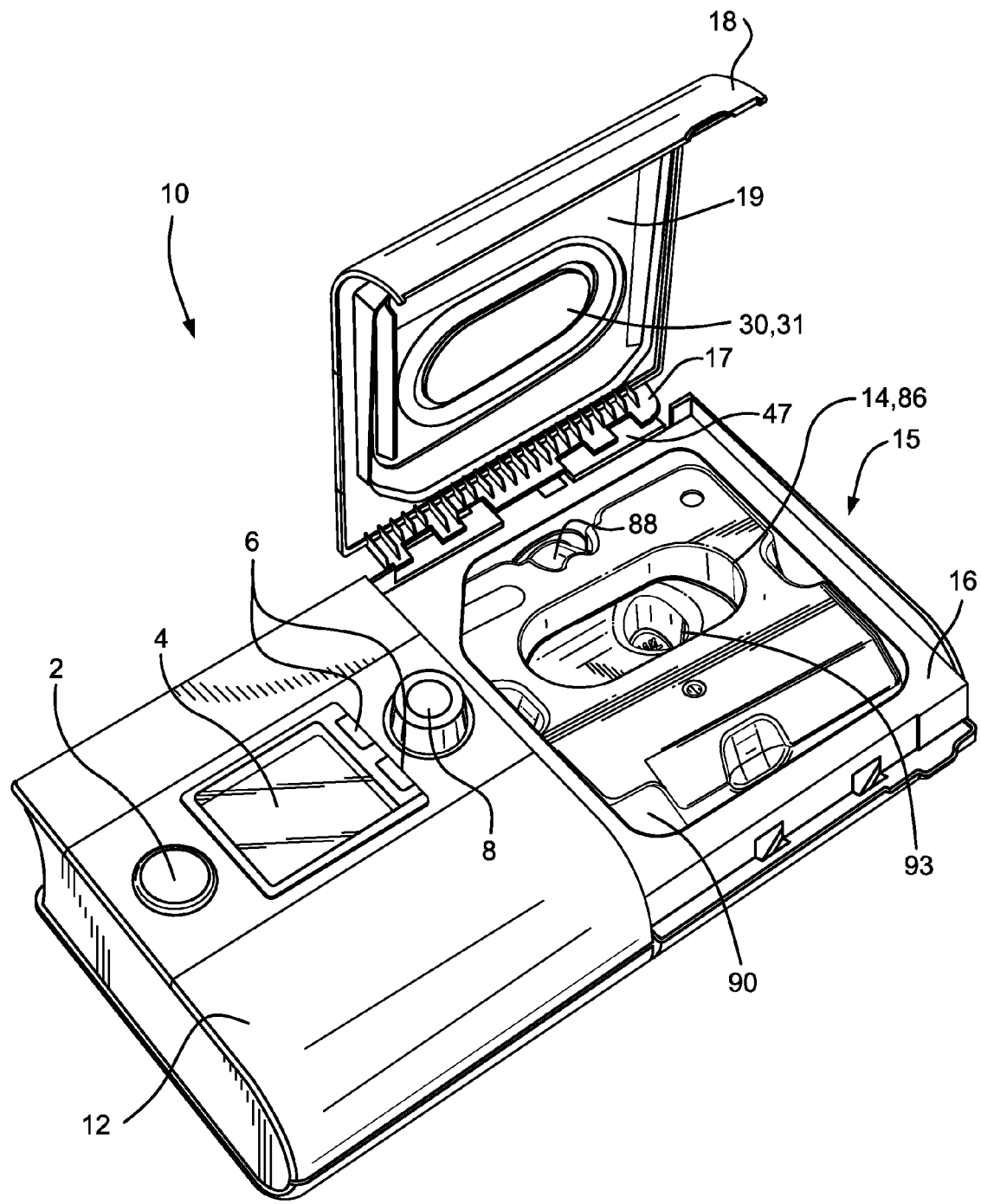
FIG. 4 schematically depicts of a PAP system including a flow generator and humidifier according to a sample embodiment.
Figure 5:
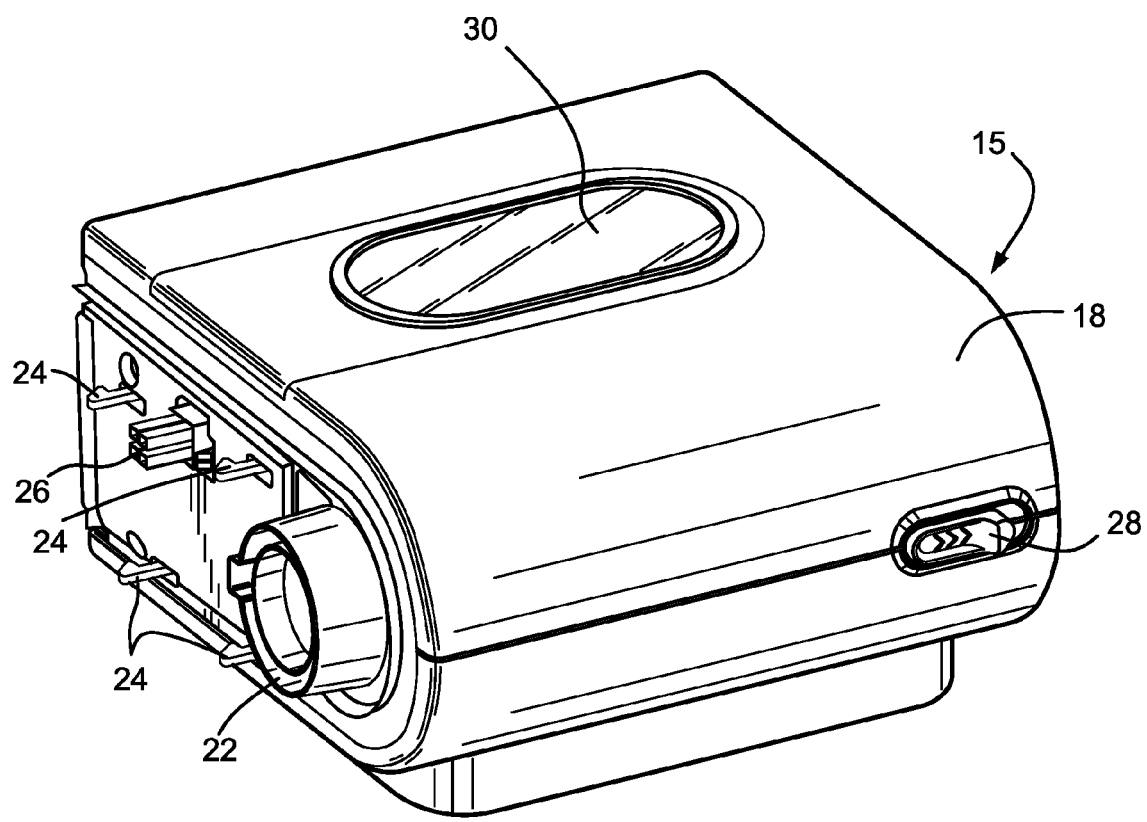
FIG. 5 schematically depicts the humidifier of FIG. 4.
Figure 6:
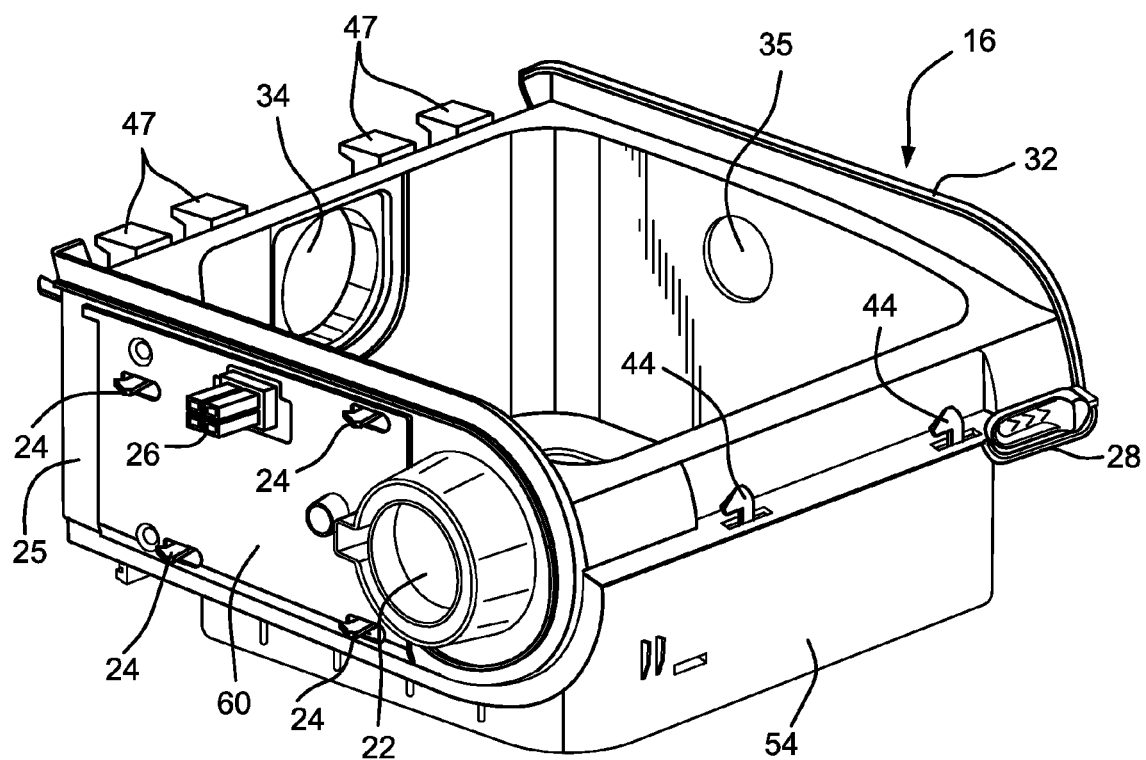
FIG. 6 schematically depicts the humidifier cradle.

Referring to FIGS. 4-6, a PAP system 10 according to a sample embodiment comprises a flow generator, or blower, 12 and a humidifier 15. The flow generator 12 is configured to generate a flow of breathable gas having a pressure of, for example, about 2-30 cm $H_2O$. The flow generator comprises a power button 2 to turn the PAP system on and off. A display 4 is provided to display interactive menus and information regarding the operation of the PAP system to the user or operator. The user or operator may select menus and/or information through inputs 6, which may be, for example, buttons or keys. A push button dial 8 may also allow the user or operator to select information and/or menus. The inputs 6 and the push button dial 8 may be used together to select information and/or menus.

The humidifier 15 comprises a humidifier chamber 16 and a lid 18 which is pivotable between an open and a closed position. A humidifier water chamber, or tub, 14 is provided in the humidifier chamber 16 and is covered by the lid 18 when the lid 18 is in the closed position. A seal 19 is provided to the lid 18. The lid 18 includes a window 30 to allow visual inspection of the contents of the humidifier tub 14. The seal 19 includes an aperture 31 that corresponds to the position of the window 30 of the lid 18. In the closed position of the lid 18, the seal 19 contacts the tub 14 to ensure good thermal contact between a bottom of the tub 14 and a heating plate (not shown) provided in the bottom of the humidifier chamber 16 as disclosed, for example, in WO 2010/031126 A1

As shown in FIGS. 4 and 5, the humidifier 15 is connectable to the flow generator 12 by connectors, or latches, 24 that engage corresponding recesses (not shown) in the flow generator 12. An electrical connector 26 is provided to electrically connect the flow generator 12 to the humidifier 15.

Figure 18:
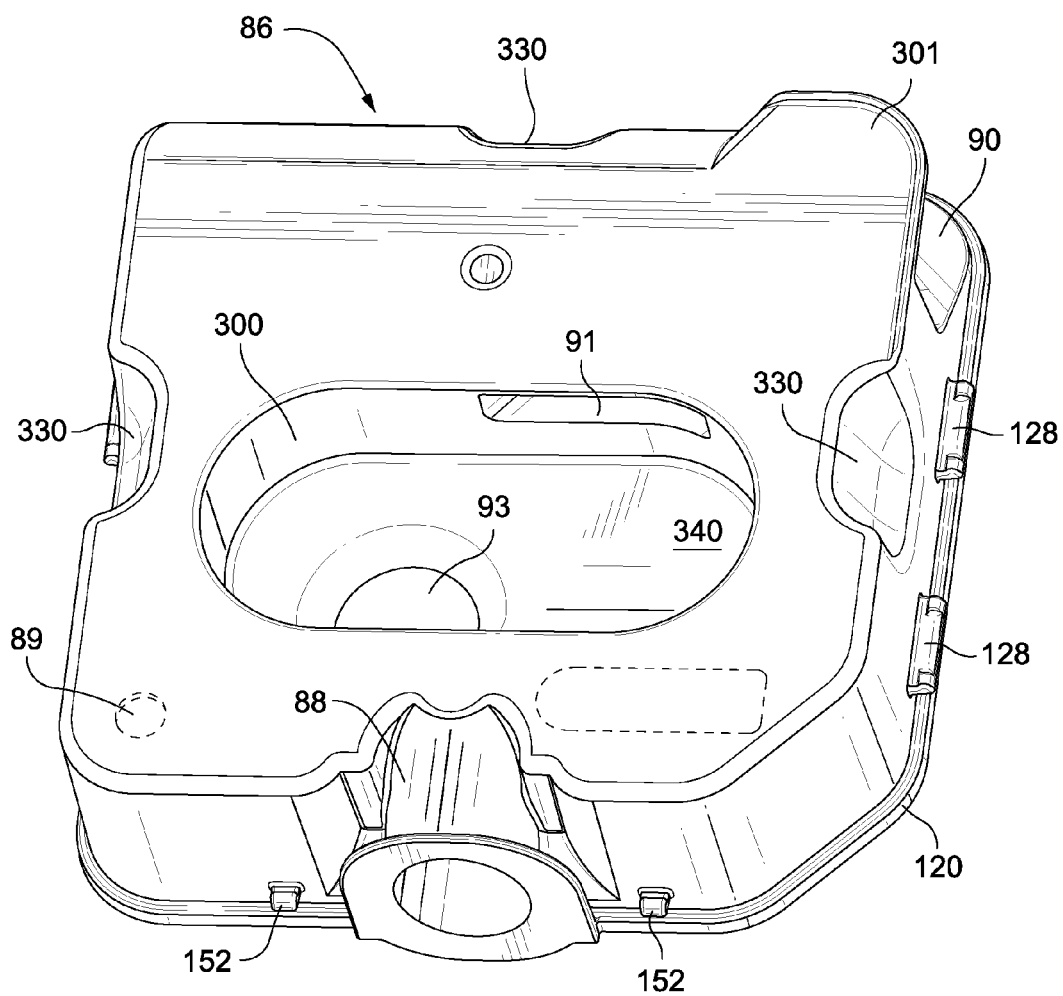
FIG. 18 schematically depicts a rear perspective view of the tub lid of FIG. 11.

As shown in FIG. 4, the tub 14 comprises a tub lid 86 that is configured to direct a flow of breathable gas generated by the flow generator 12 into a channel 90 (best shown in FIG. 7) in the tub lid 86 from a channel inlet through to a channel outlet 91 (FIG. 18) of the channel 90 into the tub 14. The humidifier chamber 16 includes an air inlet 22 configured to receive the flow of breathable gas generated by the flow generator 12 when the humidifier 15 is connected to the flow generator 12. The inlet 22 directs the flow into the channel 90 in the tub lid 86 of the tub 14. The flow is directed by the channel 90 to the inlet 93 into the tub 14. The tub 14 includes an outlet 88 for the humidified flow of breathable gas. A tube connector (not shown) may be provided at a rear portion of the humidifier 15 in communication with the outlet 88 and configured for connection to a hose, tube, or conduit that is configured to deliver the humidified flow to patient interface, e.g., a mask. It should be appreciated that the outlet 88 may be provided separately from the tub lid 86, for example it may be part of the tub base or provided as a separate element.

The humidifier 15 may include a control system, or controller, for example, a microprocessor provided on a printed circuit board (PCB). The PCB may be located in the wall of the humidifier chamber 16 and may include a light, e.g., a Light Emitting Diode (LED), to illuminate the contents of the tub 14 to permit visual inspection of the water level. Referring to FIG. 6, an aperture 35 may be provided in the wall of the humidifier chamber 16 to allow the light on the PCB to illuminate the humidifier chamber 16. The aperture 35 may be covered with a cover (not shown) to prevent access to the PCB and the light (e.g. LED) from the humidifier chamber 16. The cover may be transparent or colored to provide a colored light, such as a green light to appear within the humidifier chamber 16. The light is provided to shine into the humidifier chamber 16 to allow the water level in the water tub 14 to be seen.

It should also be appreciated that the flow generator 12 comprises a control system, or controller, that communicates with the controller of the humidifier 15 when the flow generator 12 and the humidifier 15 are electrically connected. The PAP system 10 may be operated according to various control algorithms stored in the controller(s) of the flow generator 12 and/or the humidifier 15. Such control algorithms are disclosed in, for example, U.S. Patent Application Publication 2009/0223514 A1, the entire contents of which are incorporated by reference.

The humidifier 15 comprises the humidifier chamber 16 and the lid 18 which is pivotally connected to the humidifier chamber 16. As shown in FIGS. 4 and 6, the lid 18 comprises a hinge portion 17 that is hinged to hinge portions 47 provided on the humidifier chamber 16. An opening member 28 is provided for releasing the lid 18 to allow the lid to be pivoted to the open position shown in FIGS. 4 and 6 as described in WO 2010/031126 A1. Referring to FIGS. 4 and 5, the lid 18 comprises catches (not shown) that are configured to be engaged by latches 44 to maintain the lid 18 in the closed position. The seal 19 is configured to engage the water tub 14, for example the tub lid 86, when the lid 18 is in the closed position to push the tub 14 toward an outlet 34 of the humidifier chamber 16 to assist in forming a seal between the water tub outlet 88 and the humidifier chamber outlet 34. The seal 19 is also configured to push the water tub 14 against a heating plate (not shown) when the lid 18 is in the closed position. The seal 19 is also configured to seal, when the lid 18 is in the closed position, the tub emptying aperture 89 provided in the tub lid 86.

As shown in FIG. 6, the humidifier chamber 16 comprises a humidifier cradle 32 that includes the air inlet 22. The humidifier cradle 32 also includes the humidifier chamber outlet 34 to allow the humidified flow to be delivered to a delivery hose, tube, or conduit that is configured to be connected to the humidifier to deliver the humidified flow to a patient. The outlet 34 is provided in a back side of the humidifier cradle 32. It should be appreciated that the outlet 34 may be provided on a side of the humidifier cradle 32. Such a modification would also entail modifying the tub 14 to align the outlet 88 of the tub 14 with the outlet 34 of the humidifier cradle 32.

As also shown in FIG. 6, the humidifier cradle 32 is supported by a chamber bottom 54 of the humidifier chamber 16, as disclosed in WO 2010/031126 A1

Humidifier Tub—Cleanable

Referring to FIGS. 7-27, the humidifier tub 14 comprises a tub base 82 configured to contain a supply of water and a tub lid 86 that includes a channel 90 that receives the flow of breathable gas generated by the flow generator 12 that enters the humidifier 15 through the air inlet 22. The outlet 91 of the channel 90 is configured to direct the flow into the inlet 93 of the tub lid 86 when the tub lid 86 is secured to the tub base 82 as described in more detail below. The tub lid 86 includes an opening 300 and a sump region 340 that surrounds the inlet 93 of the tub lid 86 to direct the flow of air from the flow generator to the water contained in the tub 14. The sump region 340 also facilitates filling the tub 14 by providing a larger area for entry of water than the inlet 93 of the tub lid 86. A tub emptying aperture 89 may also be provided in the tub lid 86.

FIGS. 29-38 show another example of the present technology, wherein like elements have been identified by like parts, but with a "prime", e.g., 100', added.

Figure 19:
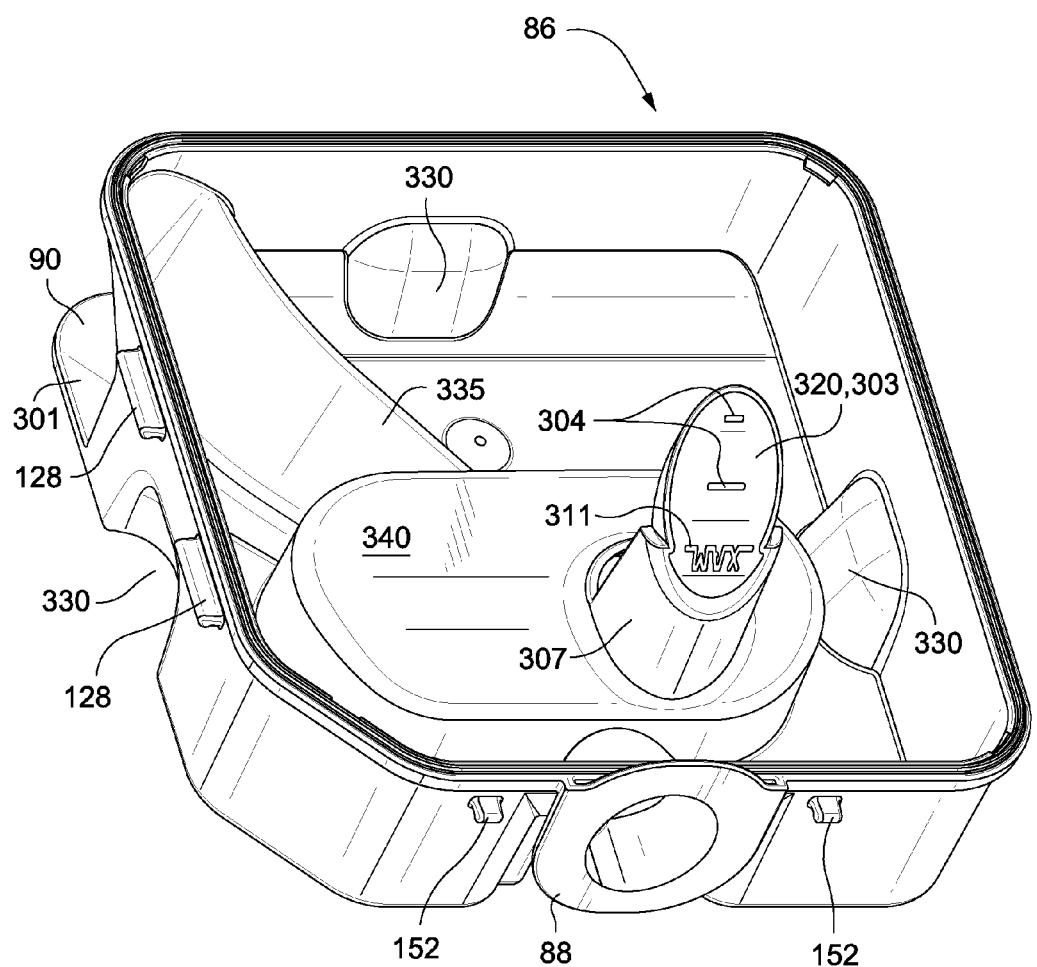
FIG. 19 schematically depicts a bottom rear perspective view of the tub lid of FIG. 11.
Figure 20:
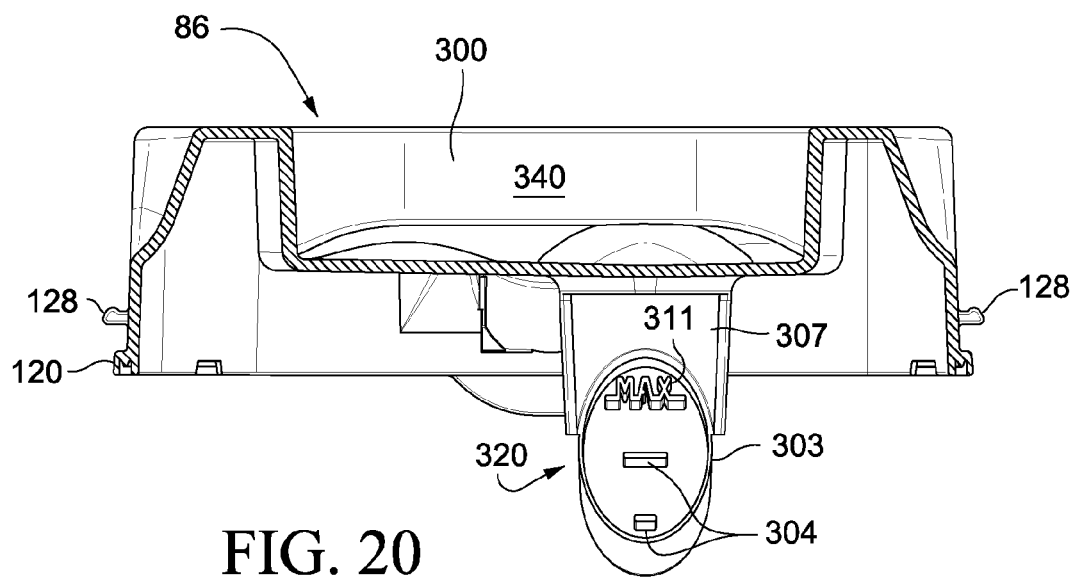
FIG. 20 schematically depicts a cross section of the tub lid of FIG. 11 along line 20-20 in FIG. 14.
Figure 21:
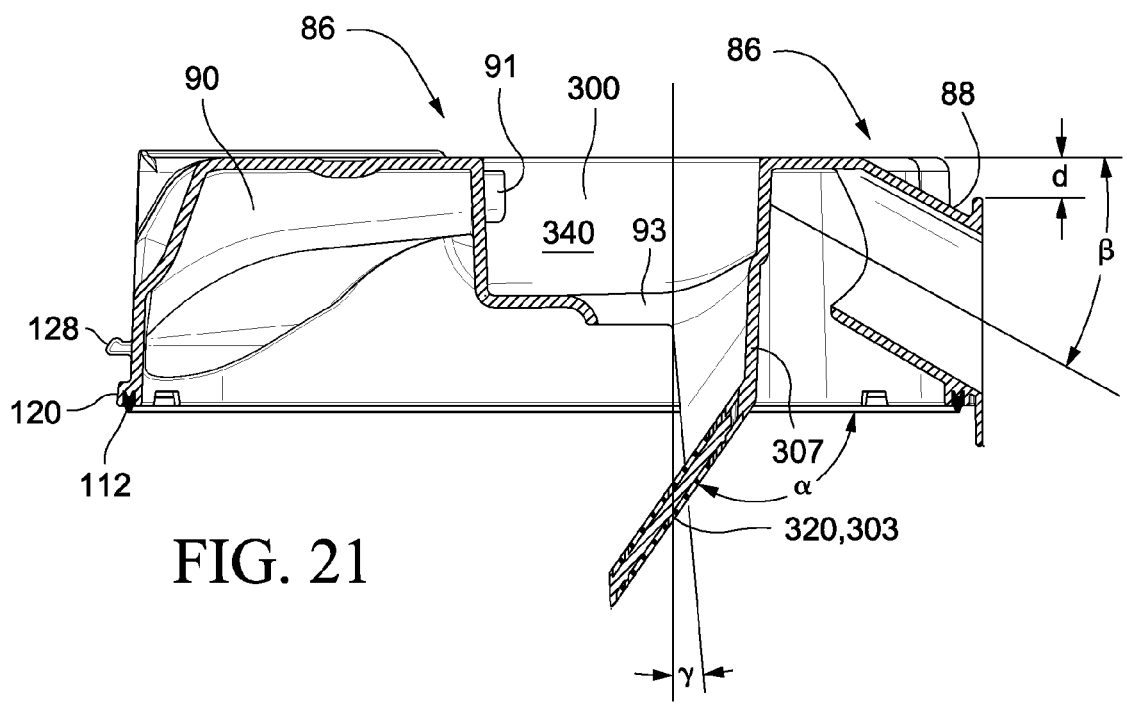
FIG. 21 schematically depicts a cross section of the tub lid of FIG. 11 along line 21-21 in FIG. 14.

Referring to FIGS. 7, 10, 11, 14, 15, 18-21, the opening 300 of the sump region 340 may be as shown, e.g. generally rectangular with D-shaped ends, or may be any other shape, for example oval, elliptical, or round. The opening 300 and the sump region 340 may be large enough to reduce the amount of water that misses the inlet 93 during filling and to buffer the water when poured in a rate that exceeds the filling capacity of the inlet 93. The inlet 93 may be provided in the bottom of the sump region 340, as shown in FIGS. 4, 7, 10, 11, 14, 15, 18 and 19, at a position that prevents water from exiting the tub 14 through the inlet 93 when the tub 14 is tilted, for example 90°, toward the flow generator 12. As shown in FIG. 21, the outlet 91 of the channel 90 is above the inlet 93 to reduce the possibility of water entering the channel 90 during filling or due to splashing.

The tub lid 86 also comprises a cover portion 301 that covers the section of the flow channel 90 from the flow generator 12 to the outlet 91 of the channel 90 that is angled down towards the flow generator 12. The cover portion 301 prevents any water from flowing back into the flow generator 12 if the tub 14 was filled with water while still connected to the flow generator 12 as water may only be poured into the tub in the region provided by the opening 300 which is designed to channel the water down towards the inlet 93 of the tub lid 86.

Figure 7:
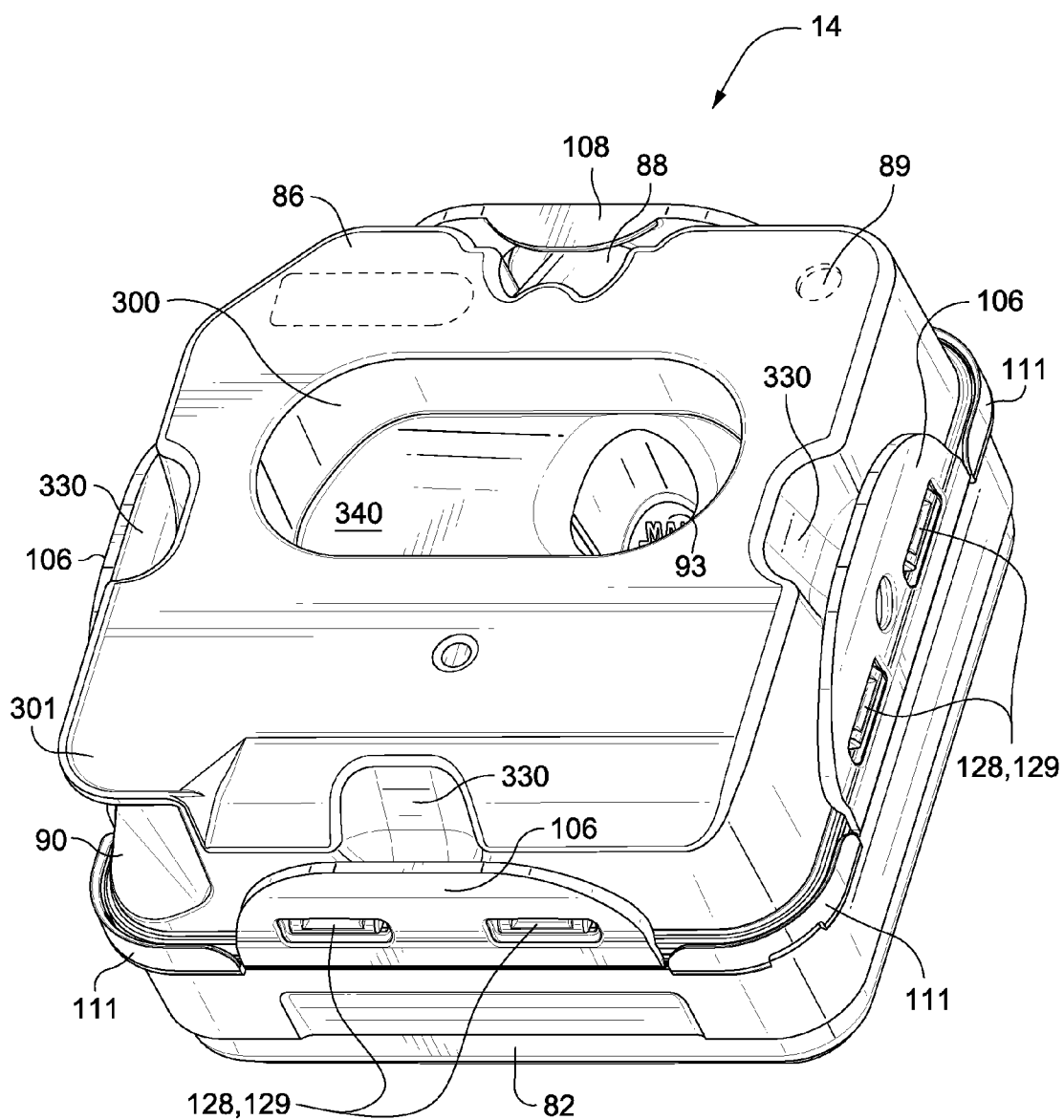
FIG. 7 schematically depicts a front perspective view of a reusable and cleanable tub according to a sample embodiment.
Figure 8:
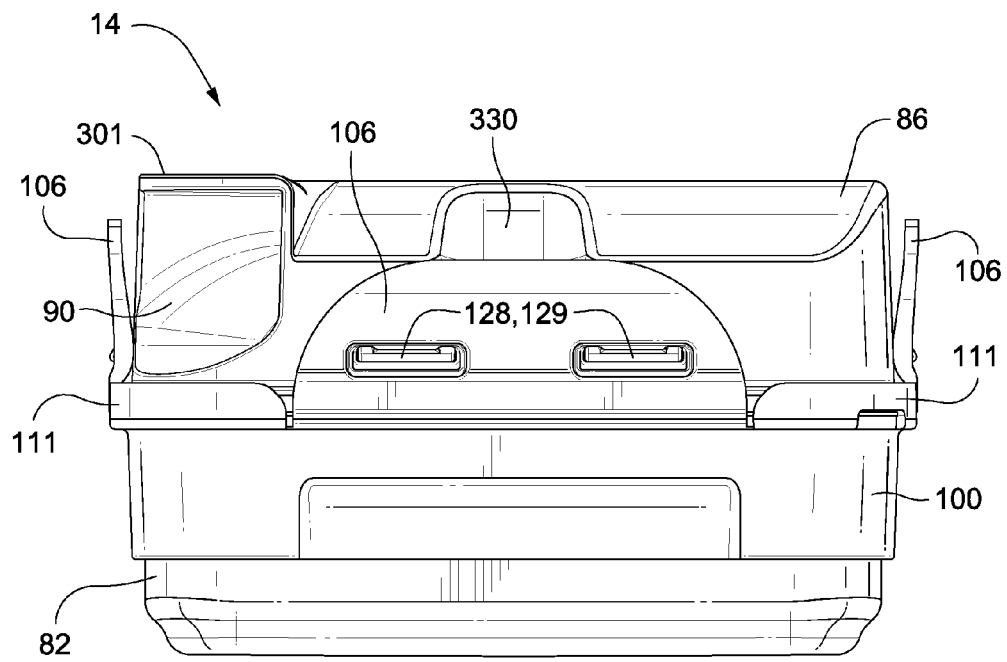
FIG. 8 schematically depicts a front side view of the reusable and cleanable tub of FIG. 7.
Figure 9:
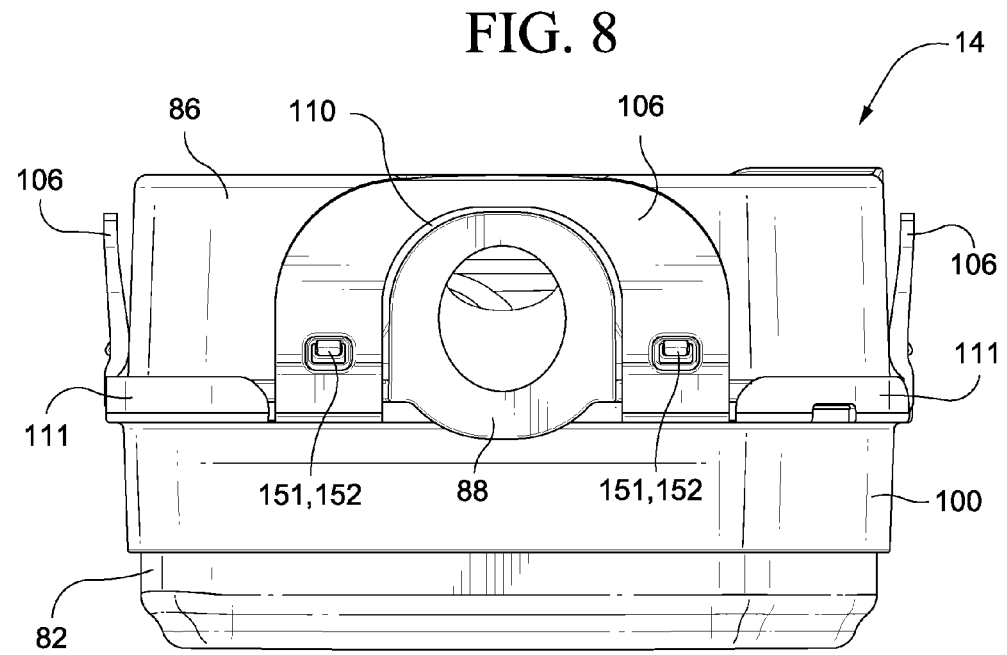
FIG. 9 schematically depicts a rear side view of the reusable and cleanable tub of FIG. 7.
Figure 10:
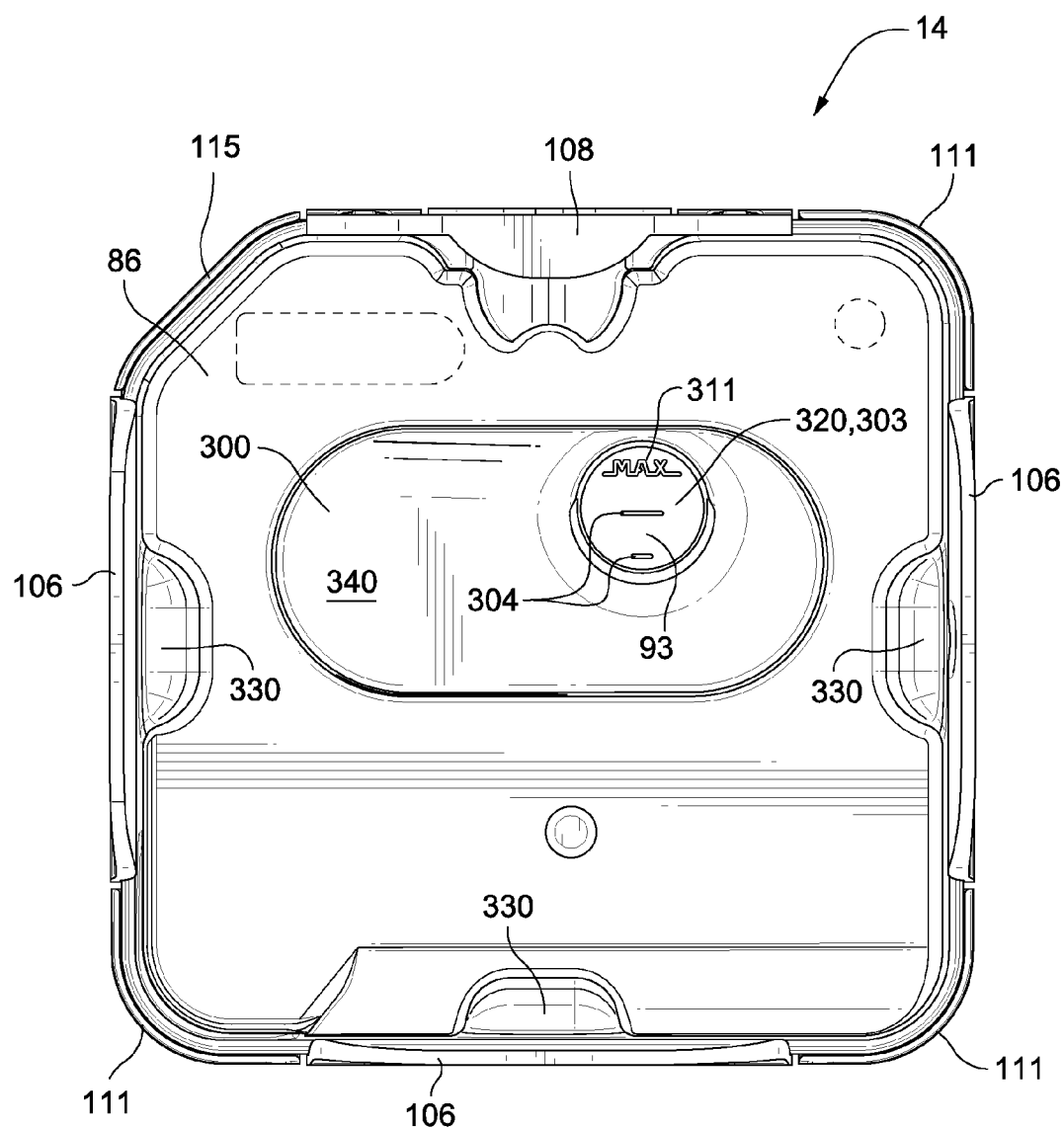
FIG. 10 schematically depicts a top view of the reusable and cleanable tub of FIG. 7.
Figure 11:
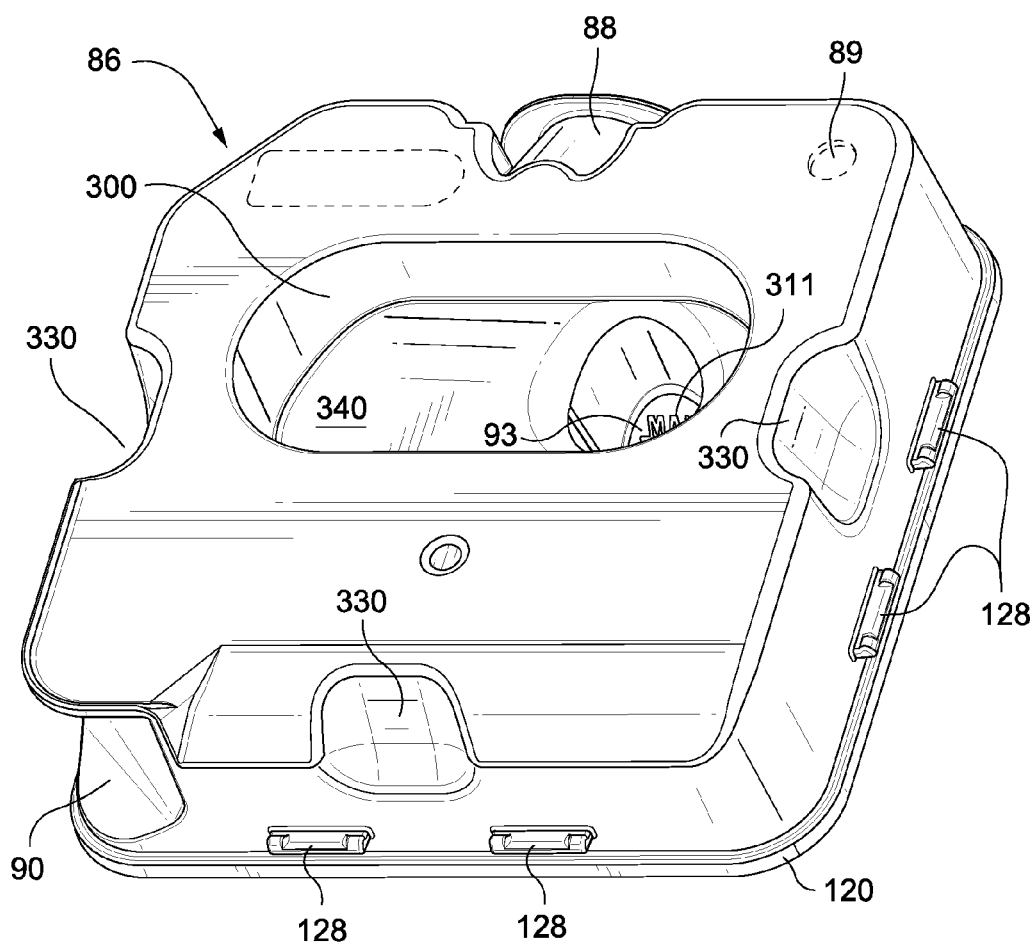
FIG. 11 schematically depicts a front perspective view of a tub top, or lid, of the reusable and cleanable tub of FIG. 7.
Figure 12:
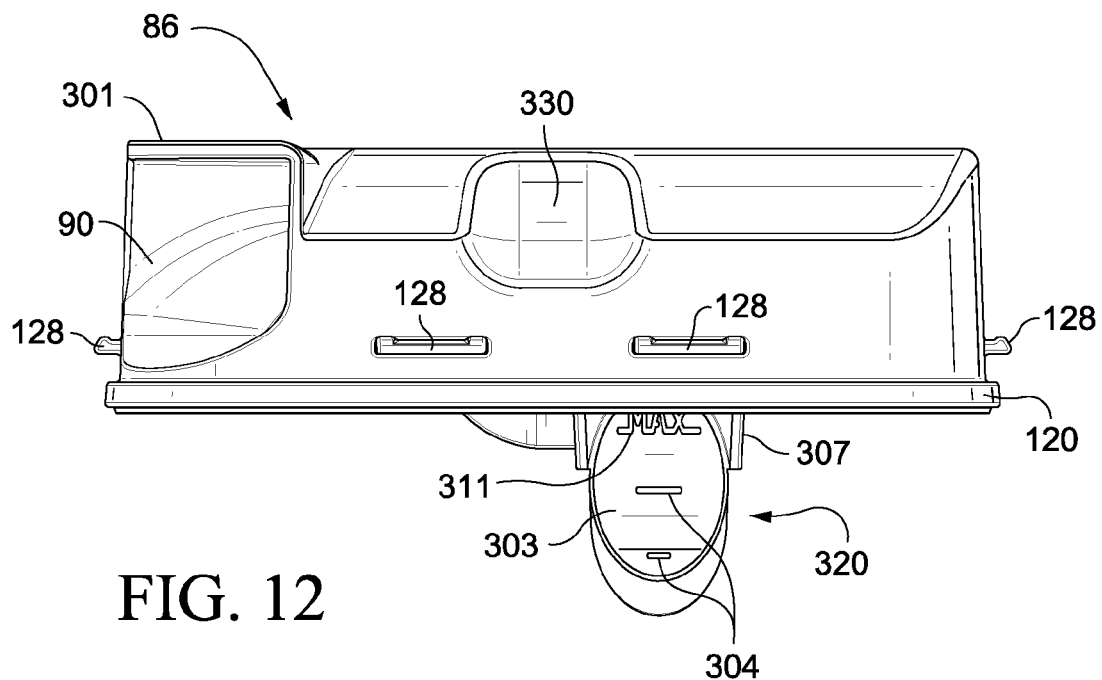
FIG. 12 schematically depicts a front side view of the tub lid of FIG. 11.
Figure 13:
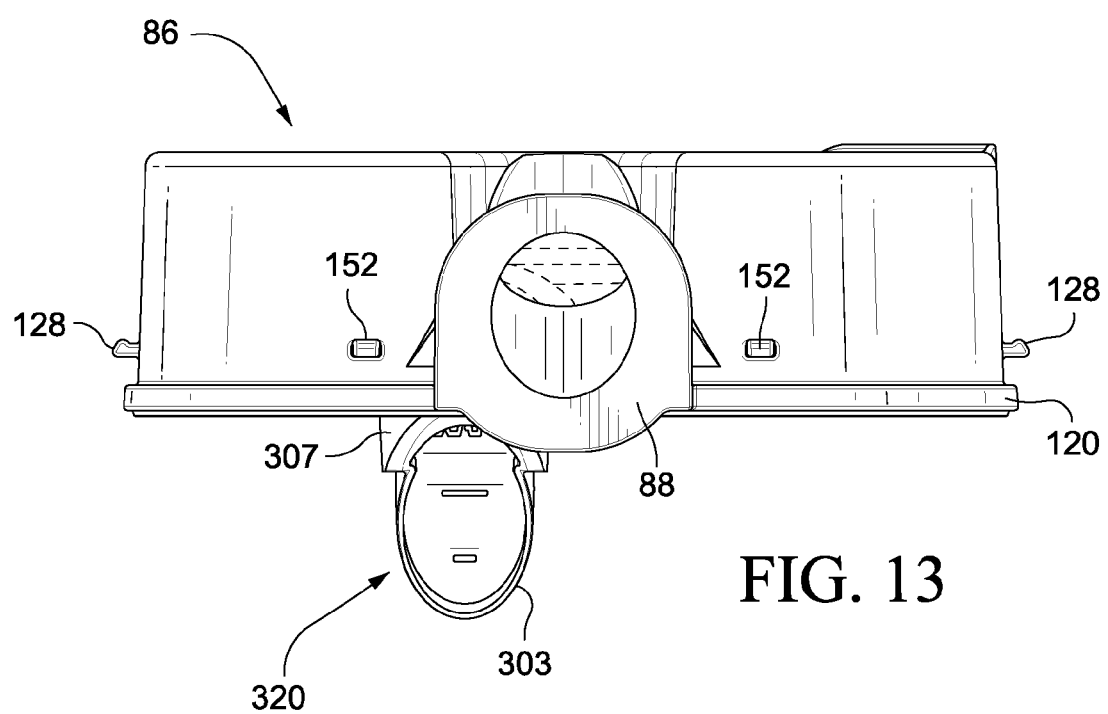
FIG. 13 schematically depicts a rear side view of the tub lid of FIG. 11.
Figure 14:
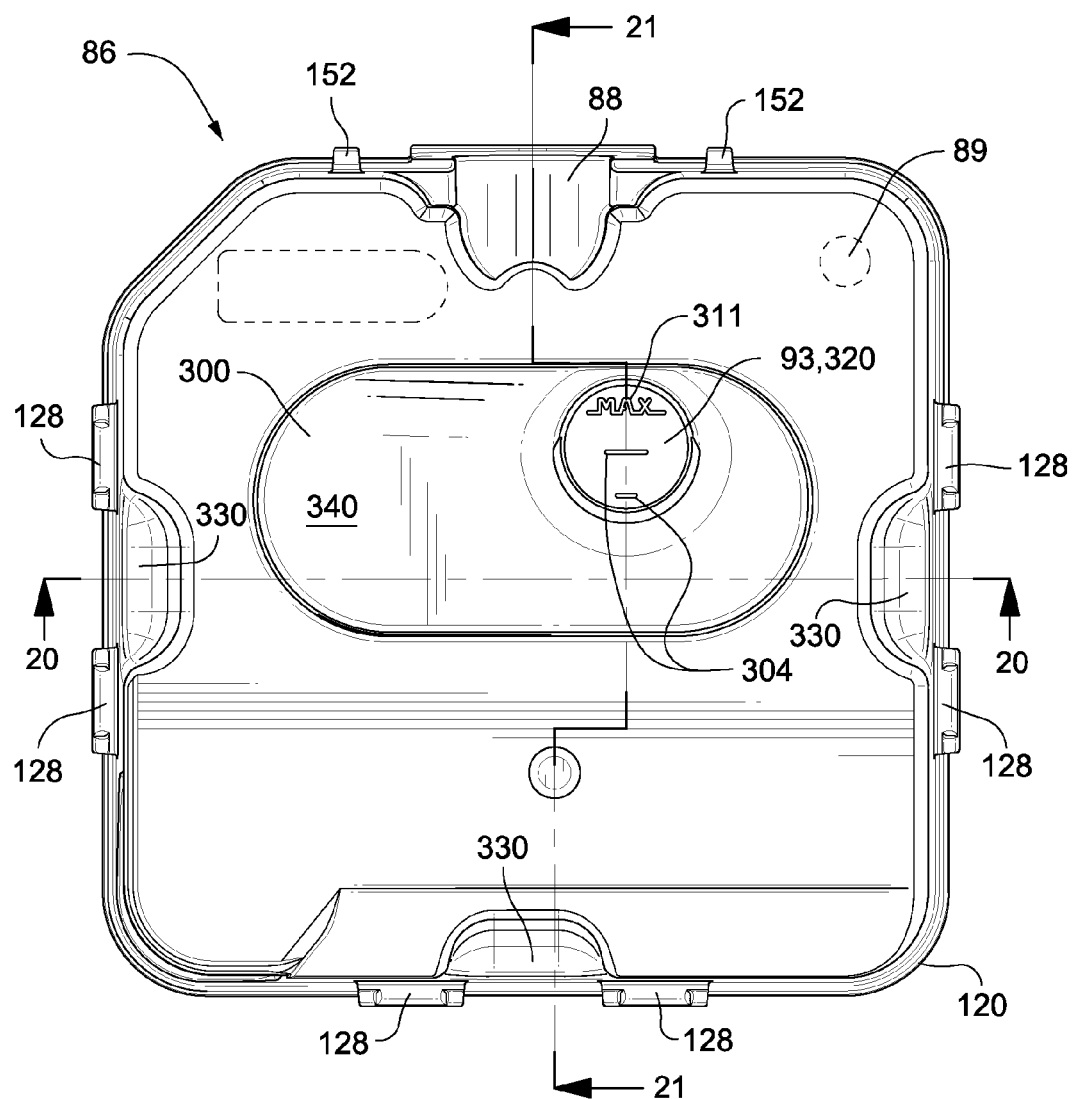
FIG. 14 schematically depicts a top view of the tub lid of FIG. 11.
Figure 15:
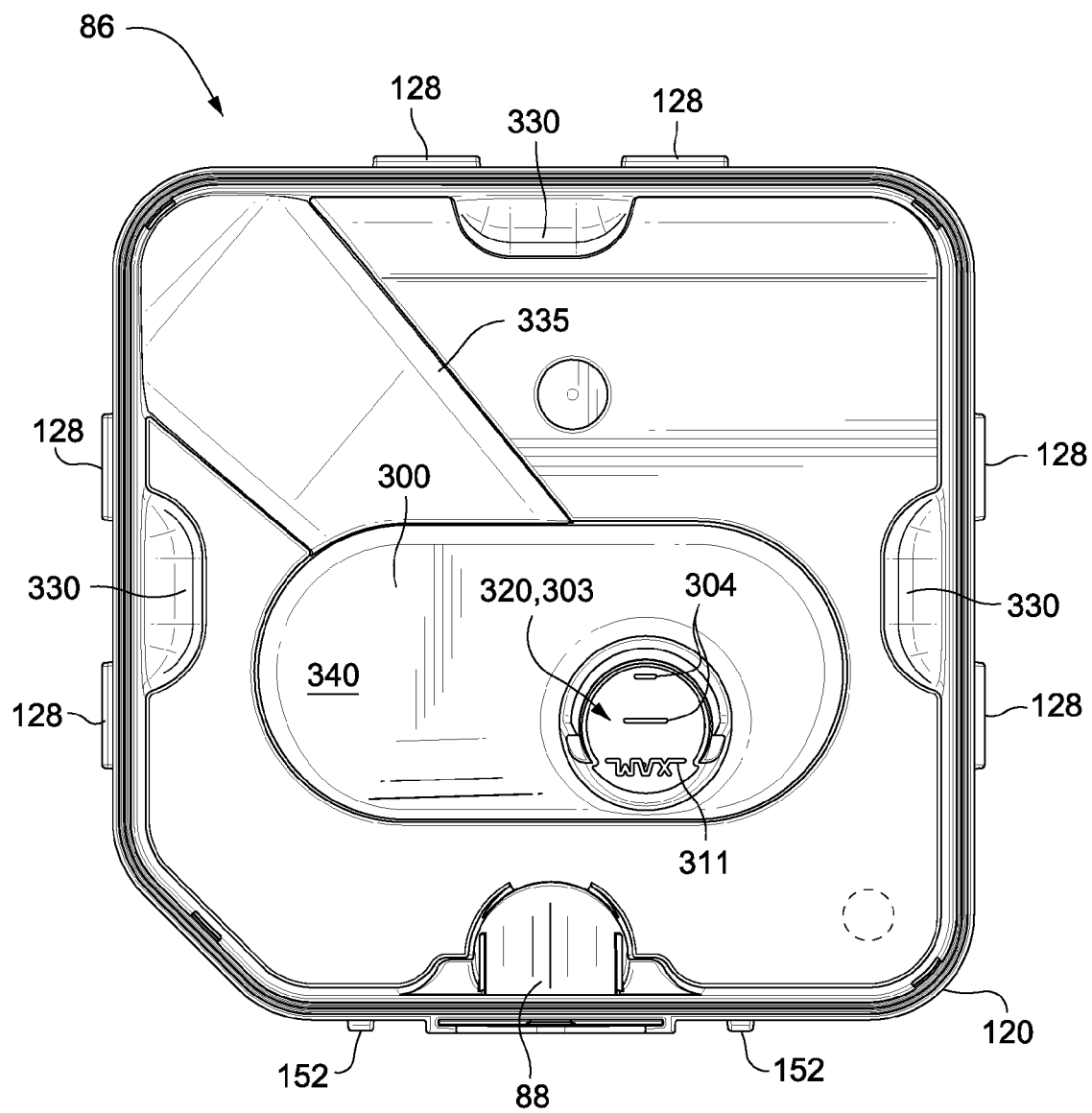
FIG. 15 schematically depicts a bottom view of the tub lid of FIG. 11.
Figure 16:
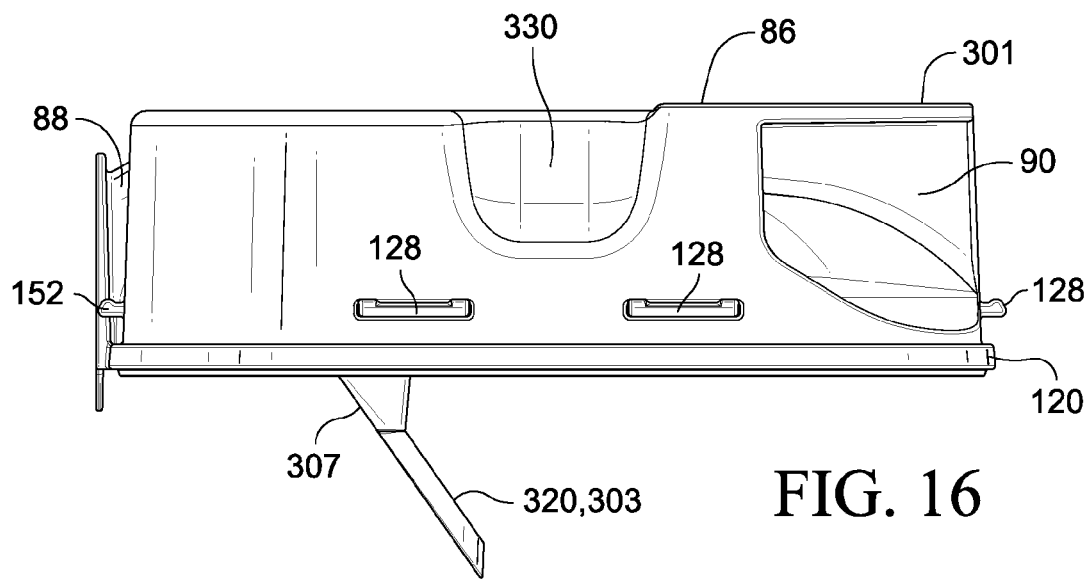
FIG. 16 schematically depicts a left side view of the tub lid of FIG. 11.
Figure 17:
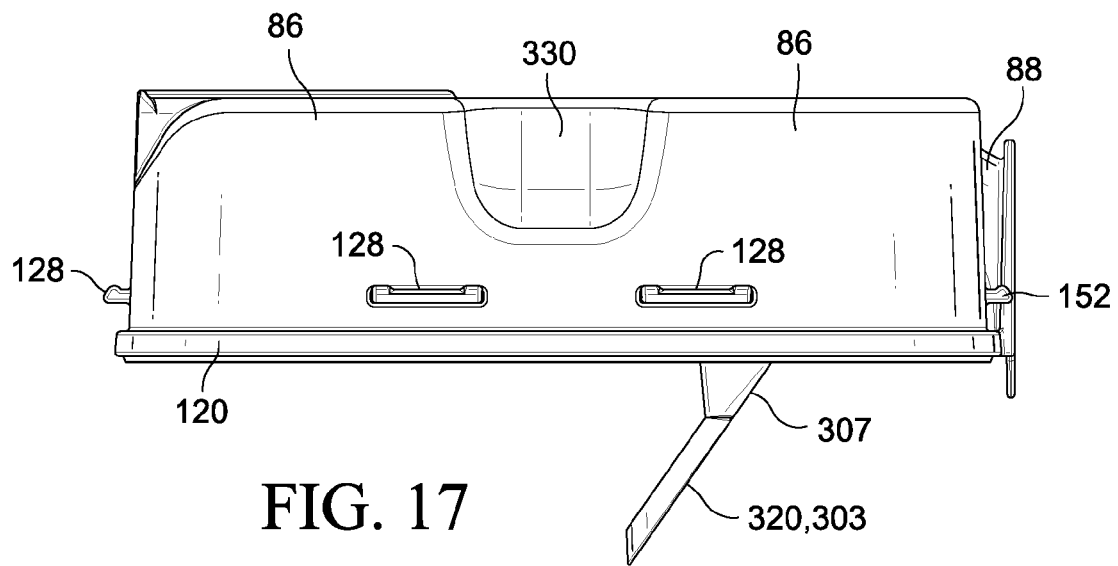
FIG. 17 schematically depicts a right side view of the tub lid of FIG. 11.

As shown in FIGS. 7-9, the tub lid 86 may be secured to the tub base 82 by a plurality of clips 106, 108 provided on a latching plate 100, although it should be appreciated that the clips 106, 108 may be provided on the tub base 82. The clip 108 may have an aperture 110 configured to accommodate the outlet 88 of the tub 14. The tub lid 86 may include projections 128 that are received in apertures 129 in the clips 106. The tub lid 86 may also include projections 152 that are received in apertures 151 provided in the clip 108.

As also shown in FIGS. 7-9, the tub lid 86 may include recesses 330 to accommodate the fingers of a user of the tub or a clinician to provide a space between the tub lid 86 and the clips 106 as the user inserts the tub lid 86 on to the tub base 82 so that the projections 128 are received in the apertures 129. The recesses 330 may also accommodate the fingers during removal of the lid 86 from the base 82, for example to allow the parts of the tub 14 to be disassembled and cleaned.

Referring to FIGS. 22-25, the latching plate 100 comprises the clips 106, 108 that may be integrally formed with the latching plate 100 by, for example, living hinges 125. The latching plate 100 may be formed of, for example, polypropylene (PP) which will allow the living hinges 125 to be open and closed a large number of times without breaking. Polypropylene is also inexpensive and has good chemical resistance and is a sturdy and tough material that is not brittle.

Figure 22:
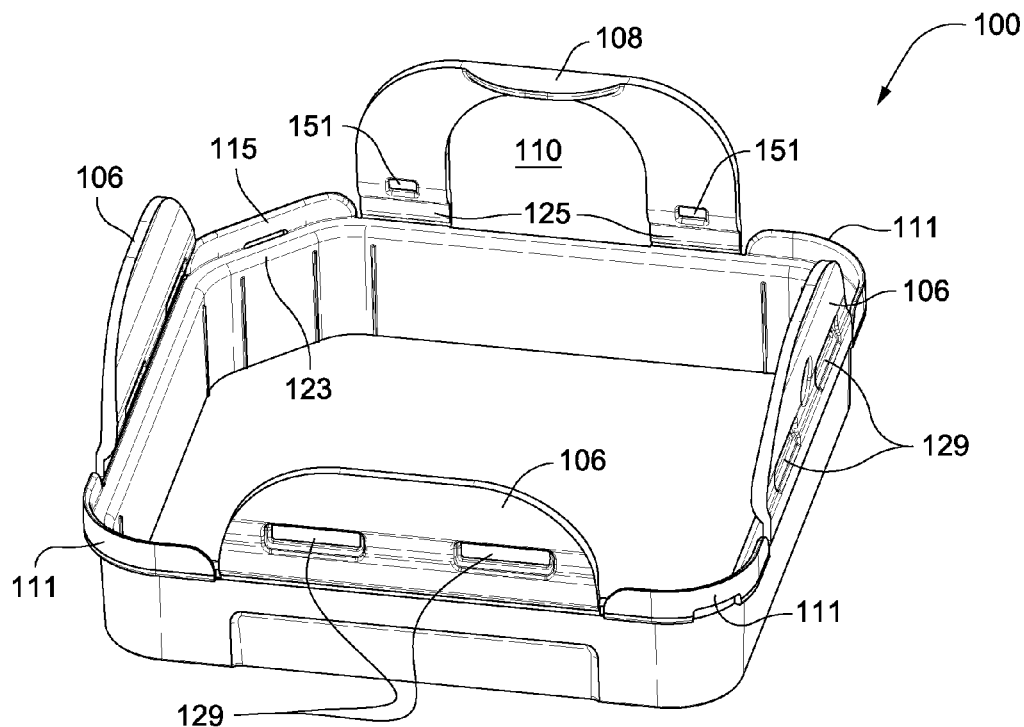
FIG. 22 schematically depicts a latching plate according to a sample embodiment in a "closed" position or configuration.
Figure 23:
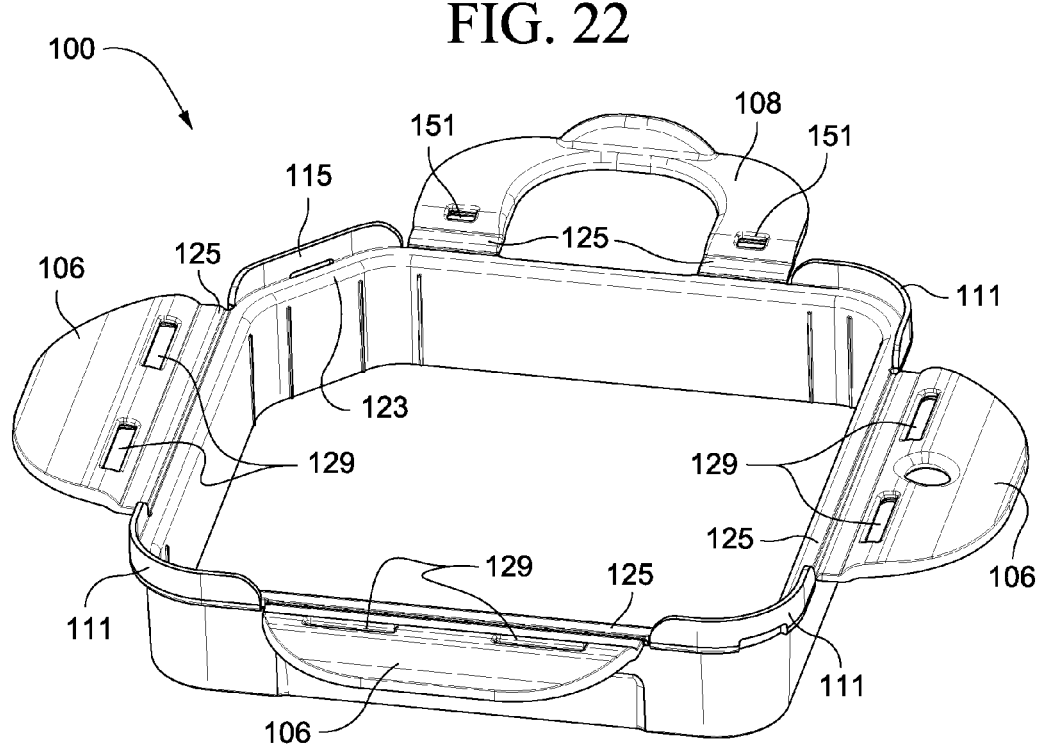
FIG. 23 schematically depicts the latch plate of FIG. 22 in an "open" configuration.

FIG. 22 shows the latching plate 100 with the clips 106, 108 in a "closed" position or configuration that retains the tub lid 86 to the tub base 82 and FIG. 23 depicts the latching plate 100 in an "open" configuration with the clips 106, 108 folded downwardly to permit insertion of the tub base 82 into the latching plate 100 as described in more detail below.

Figure 24:
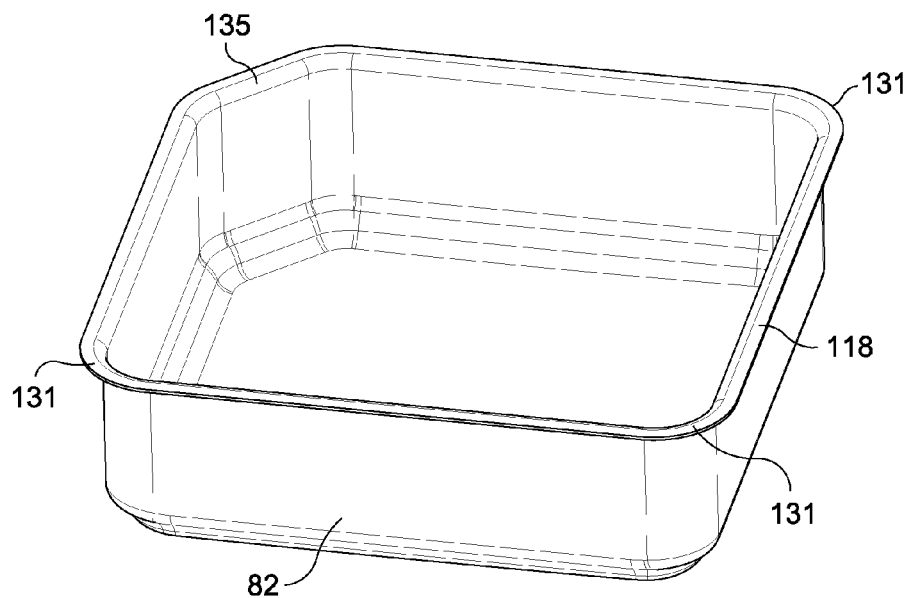
FIG. 24 schematically depicts the tub base.
Figure 25:
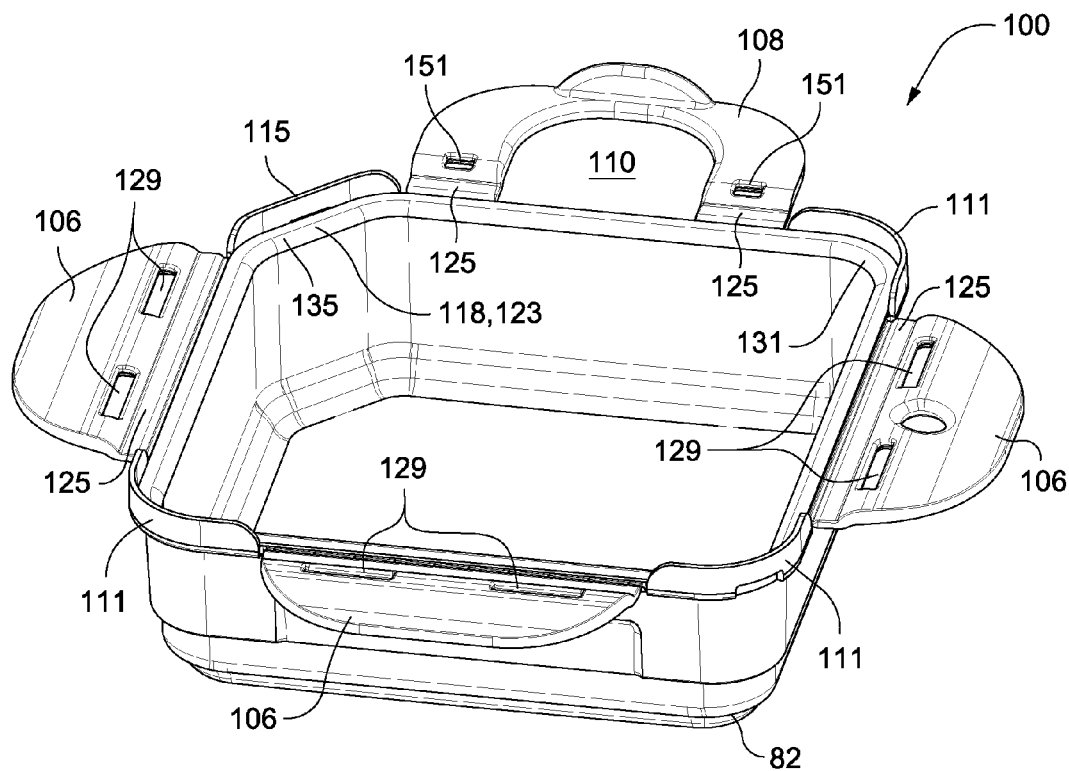
FIG. 25 schematically depicts the tub base and latching plate in a connected configuration.

As shown in FIGS. 22 and 23, the latching plate 100 includes corner flanges 111, 115 that extend from a rim 123 of the latching plate 100. As shown in FIG. 24, the tub base 82 comprises corresponding corners 131, 135 that facilitate alignment and assembly of the tub base 82 with the latching plate 100, as shown in FIG. 25. The latching plate 100 is slid into place from the bottom of the tub base 82 so that the rim 123 of the latching plate 100 engages with, i.e. overlies, the rim 118 of the tub base 82. The latching plate 100 is engaged with the tub base 82 by a friction fit (and this fit can be enhanced, e.g., by heating the plate to an elevated temperature and assembling these parts at that time) so that the latching plate 100 is retained when the clips 106, 108 are in the open configuration shown in FIG. 25. The tub lid 86 is connected to the tub base 82 and secured in position by folding the clips 106, 108 from the open position shown in FIG. 25 to the closed position shown in FIG. 7. The humidifier tub 14 may then be inserted into the humidifier 15 as shown in FIG. 4.

Water Level Indicator

Referring to FIGS. 10-21, a water level indicator 320 may be provided to the tub lid 86 of the humidifier tub 14 that is visible through the window 30 of the lid 18 of the humidifier 15. The light emitted from the PCB through the aperture 35 may improve the visibility of the water level on the water level indicator 320. The water level indicator 320 may comprise a base portion 307 that extends from the tub lid 86 around the inlet 93 and an angled or inclined portion 303 extending from the base portion 307. The inclined portion 303 may include markings 304 to indicate various water levels. The inclined portion 303 may also include indicia 311 (e.g. "MAX") to indicate a maximum water fill level.

Figure 38:
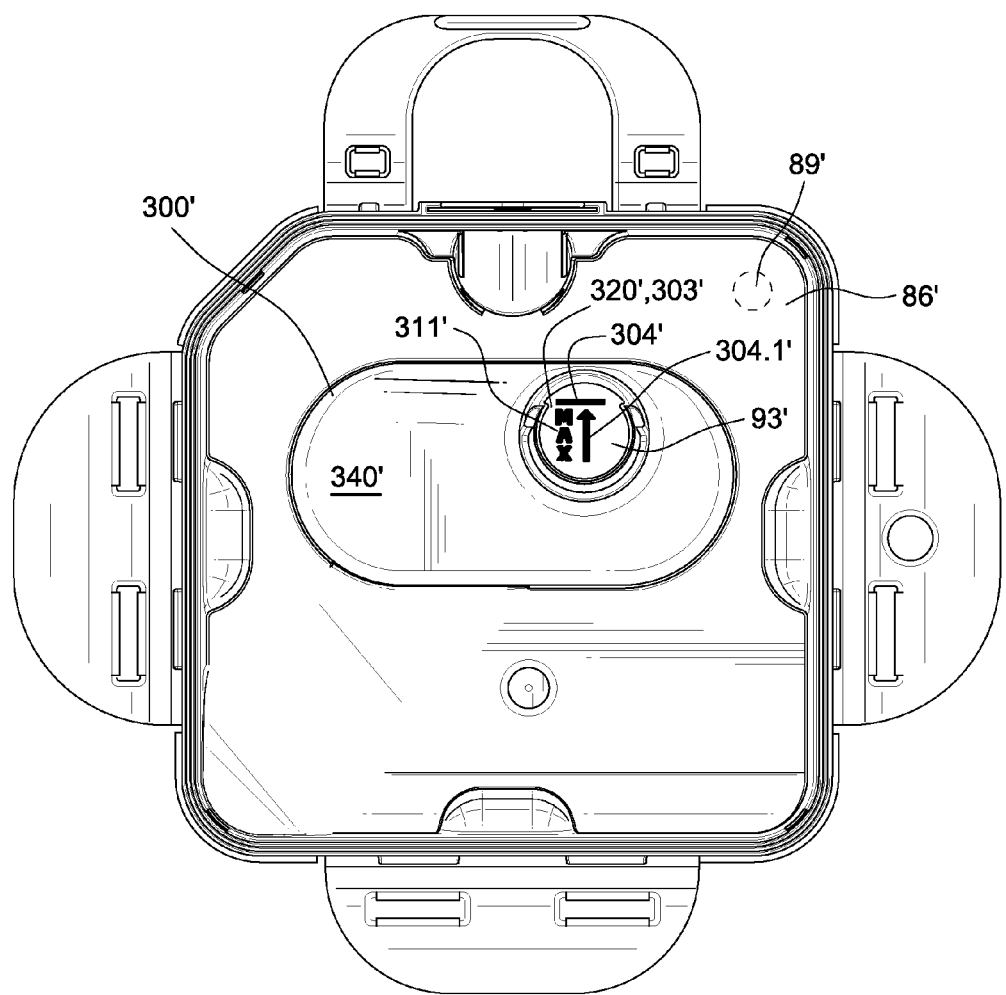

In the case of FIG. 38, the indicator 320' may include a marking 304' (e.g., indicating the maximum fill level), and the indicia (e.g., wording such as "MAX") may be written in a vertical orientation such that the indicator becomes progressively covered with water as the tub base is filled, e.g., the "X" in "MAX" is first covered then the "A", then the "M" before reaching the fill line. Further, the lettering in the indicia may be dimensioned so that the individual letters increase (or decrease) in size in a direction towards the bottom of the tub. One or more of these measures should help the user better anticipate when the water level is approaching the maximum fill level, to prevent water from inadvertently overflowing. To this end, a vertically oriented line including an arrow 304.1' at its top end also indicates the direction of filling. The marking, indicia and/or wording may be placed and formed so that it is depressed into, projects from and/or is in-plane with its support surface.

As shown in FIGS. 19-21, the water level indicator 320 may be integrally formed with the tub lid 86, e.g., the base portion 307 may be formed in one piece with the tub lid 86 via a molding process. Optionally the base portion 303 may extend half way around the inlet. This provides ease of manufacturing and assembly and reduces costs by reducing the number of components of the humidifier tub 14. For example, the flow plate disclosed in WO 2010/031126 A1 may be eliminated from the tub. It should be appreciated, however, that the water level indicator 320 may be formed separately from the tub lid 86 and be attachable to, and detachable from, the tub lid 86.

As the water level indicator 320 is located adjacent the water and airflow inlet 93, a user can immediately see from the top, while pouring water into the sump region 340, when the water level has reached a desired level, and/or the maximum level. This improves usability compared to, for example, a water level indicator that is located at a position distant from the water inlet 93 that must be looked at and checked separately from the filling process, or as a water line on the side of the tub as a user would have to tilt his or her head to determine the water level or look lower down at the side to see if water has filled to the desired or maximum level. In addition, when the tub 14 is placed inside the humidifier 15 and the lid 18 is closed to form a pressurised chamber, the window 30 allows a user or clinician to look from the top through the window 30 to see the tub 14 inside the humidifier 15. The location of the inlet 93 and the water level indicator 320 is beneath the window 30 so the user or clinician can easily and immediately check the water level without having to open the lid 18 and/or take out the tub 4. A user or clinician who suspects that the water has run out can visually check without stopping or disturbing the operation of the system. Reducing the need to remove the tub 14 from the humidifier 15 also allows the user or clinician to check water level without risking spillage of the water from the tub 14 and/or into the flow generator 12.

The inclined portion 303 of the water level indicator 320 baffle is located generally in front of the outlet 88 of the tub 14. This helps to deflect water away from the outlet 88 while filling the tub 14 by pouring water into the sump region 340. Also, as the water inlet 93 is also the air inlet, when the airflow enters the interior of the tub 14, it is deflected generally away from the outlet 88, thus directing the airflow across the water surface before exiting the outlet 88. As the pressurized air inflow is initially directed away from the outlet 88 there is less chance of splashing or spitting of water out of the outlet 88. The shape, angle of incline, and location of the inclined portion 303 of the water level indicator 320 may be designed to provide a desired airflow profile to improve water vapour pickup by the airflow and to reduce the likelihood of water spitting or splashing out of the outlet 88. The outlet conduit 88 may be angled upwards and the inclined portion 303 of the water level indicator 320 may be inclined to direct the pressurised airflow to not hit the water surface directly. A wall 335 may also be provided in the tub lid 86 to direct the airflow.

The water level indicator 320, for example, the inclined portion 303, may be formed of a colored plastic material, for example yellow. The water level indicator 320 may be, for example, translucent. When the tub 20 is filled with water, the water level indicator 320 may appear to change color, for example appearing slightly darker or a greenish-yellowish color as the water level rises.

As shown in FIG. 21, the inclined portion 303 may be at an angle α to a bottom plane of the tub lid 86. The value of the angle α may depend on a combination of factors, including the size of the inlet 93, the length of the inclined portion 303, the depth of the tub base 82, and/or the distance the inclined portion 303 extends into the tub base 82 and/or water. The angle α may be from just over 90° to just under 180°. The angle α should be sufficient to permit the inclined portion 303, including the indicia, to be visible from generally above the tub, while not causing the inclined portion 320 to extend further than the radial length of the inlet 93. That is, the inclined portion 303 should not extend under the portion of the sump region 340 surrounding the inlet 93 as such an overlapping of material (i.e. the inclined portion 303 and the sump region 340) increases the moulding and tooling complexities associated with forming the tub lid 86 as a single piece. The angle may be, for example, about 115°-135°, for example about 125°. The angle α should improve the visibility of the indicia, for example by increasing the contrast of the colour of the indicia with the water level when viewed from above. The angle α should also allow the inclined portion 303 to extend deep enough into the tub base 82 to allow indication of the water level until it is quite low. The combination of the angle α and the length of the inclined portion 303 may be chosen to provide these results.

The angle α may also be designed so that the change in the air flow direction causes only a small increase in total pressure loss through the tub and so that a swirling action is created in the air flow due to the inclined portion 303 in combination with other internal tub features, e.g., wall 335. The swirling versus pressure loss determination may be made using, for example, computational fluid dynamics (CFD) simulation.

As also shown in FIG. 21, the base portion 307 of the water level indicator 320 may be provided at an angle γ to a vertical axis of the tub. The angle γ may be, for example about 1°-10°, for example about 5°. The angle γ may improve water flow from the inlet 93 and swirl of the air flow over the surface of the water.

The outlet 88 has an axis at a downward angle β to the plane of the top of the humidifier lid 86. The angle β may be, for example, about 25°-35°, for example about 29.5°. The top of the outlet 88 is also displaced a distance d from the top of the humidifier lid 86 that may be, for example, about 1 mm-10 mm, for example about 5.6 mm. The downward angle and displacement of the outlet 88 helps to prevent spill back of water from the tub.

As shown in the figures, the water level indicator 320 may be a rounded D-shape, although it should be appreciated that other shapes such as rectangular, square, triangular, oval or any other shape may be used.

The tub base 82 may be formed of, for example, metal. For the cleanable and reusable tub 14, the tub base 82 may be formed of stainless steel. For a cleanable and disposable tub, the tub base may be formed of a lower cost conductive material such as aluminium or conductive polymers. It should be appreciated that the tub base 82 may be formed of other metals or alloys, or of other materials.

The tub lid 86 may be formed of, for example, a plastic material, such as polycarbonate. For example, the tub lid 86 may be formed of Makrolon 2458, manufactured by Bayer. For a cleanable and reusable tub, the tub lid may be formed of a dishwasher and/or disinfection safe material, such as polycarbonate. For a disposable tub, the tub lid may be formed from a lower cost material, such as ABS (acrylonitrile butadiene styrene). The tub lid 86 may be transparent, e.g. water clear, or may be translucent, including any colour of translucent material.

Humidifier Tub—Disposable

Figure 28:
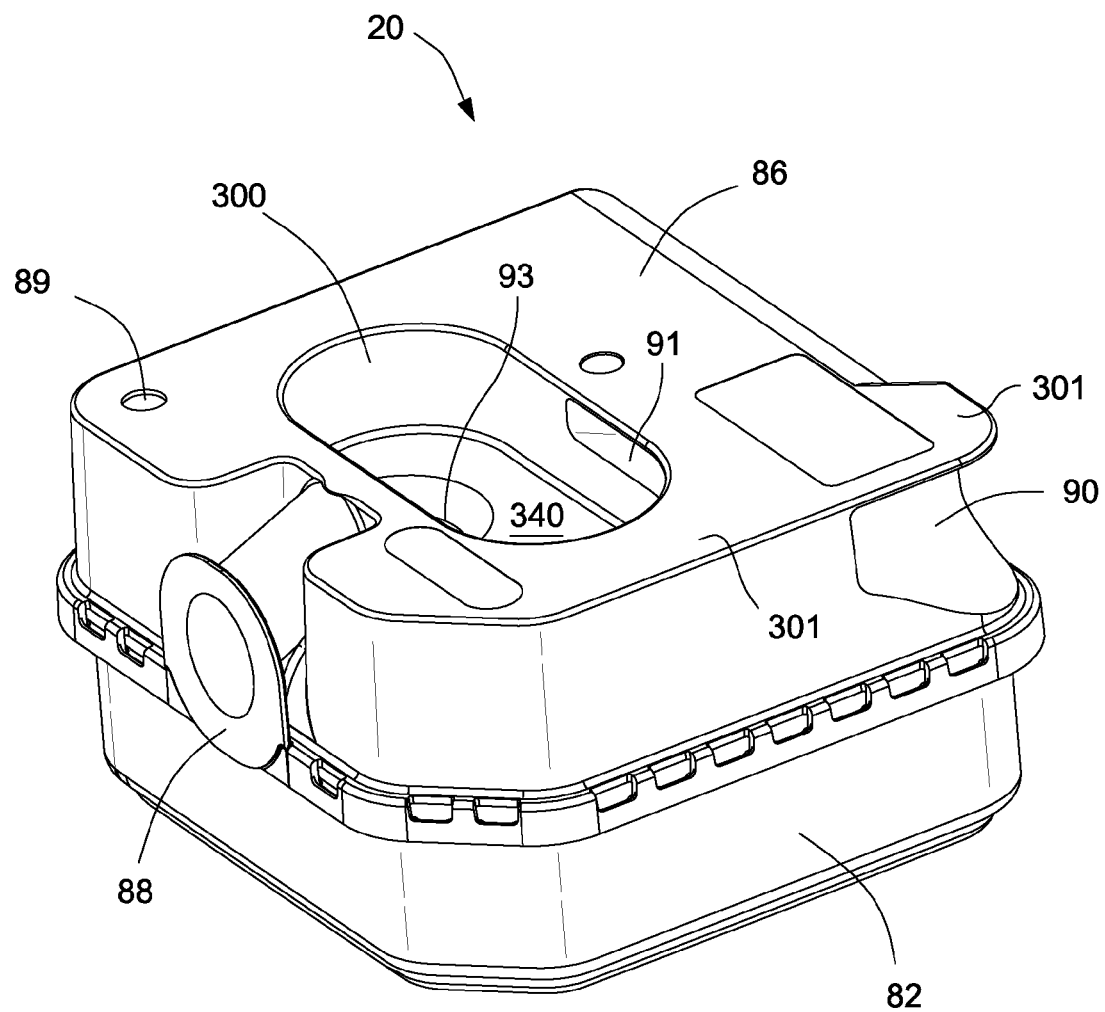
FIG. 28 schematically depicts a rear perspective view of a disposable tub according to a sample embodiment.
Figure 29:
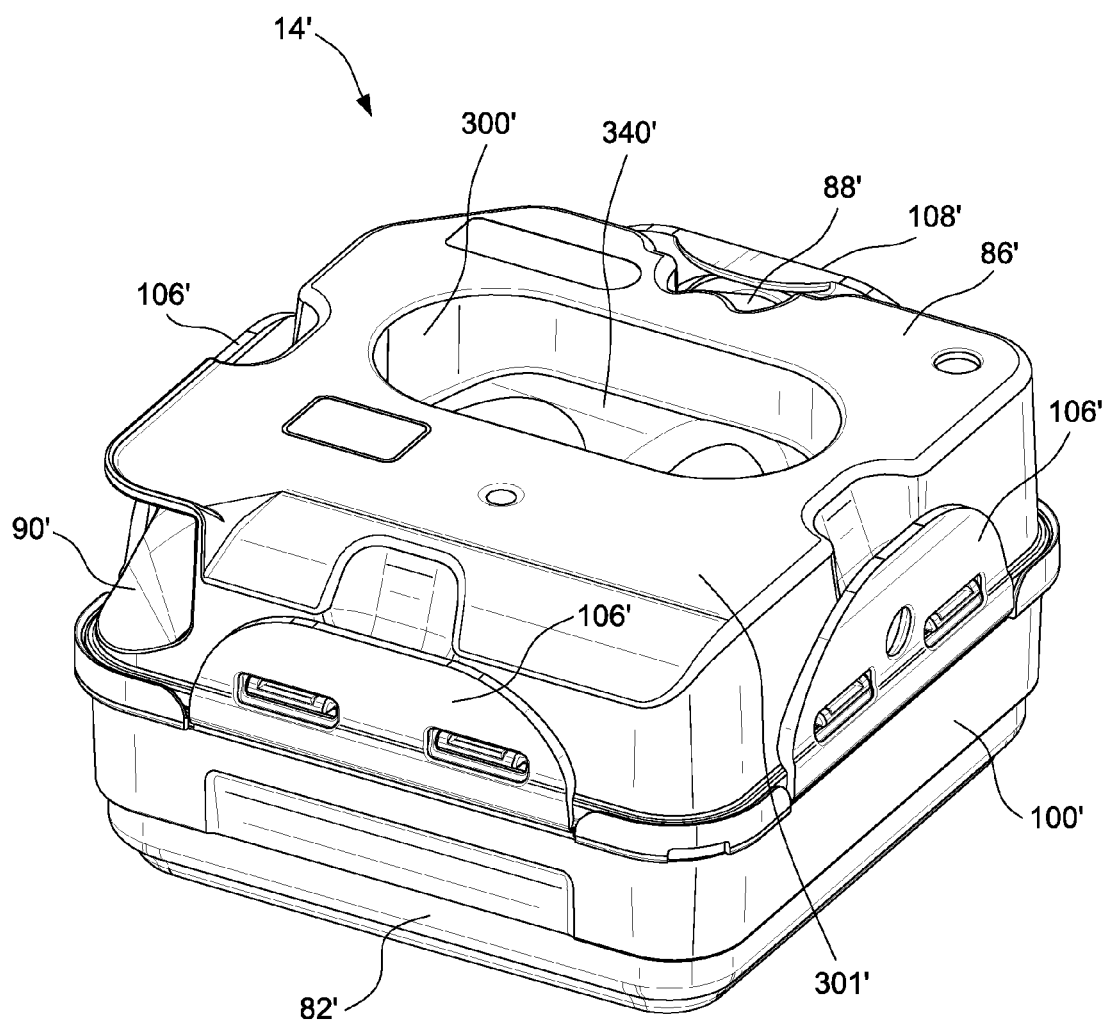
FIGS. 29-38 depict a reusable and cleanable tub according to another example of the present technology.
Figure 30:
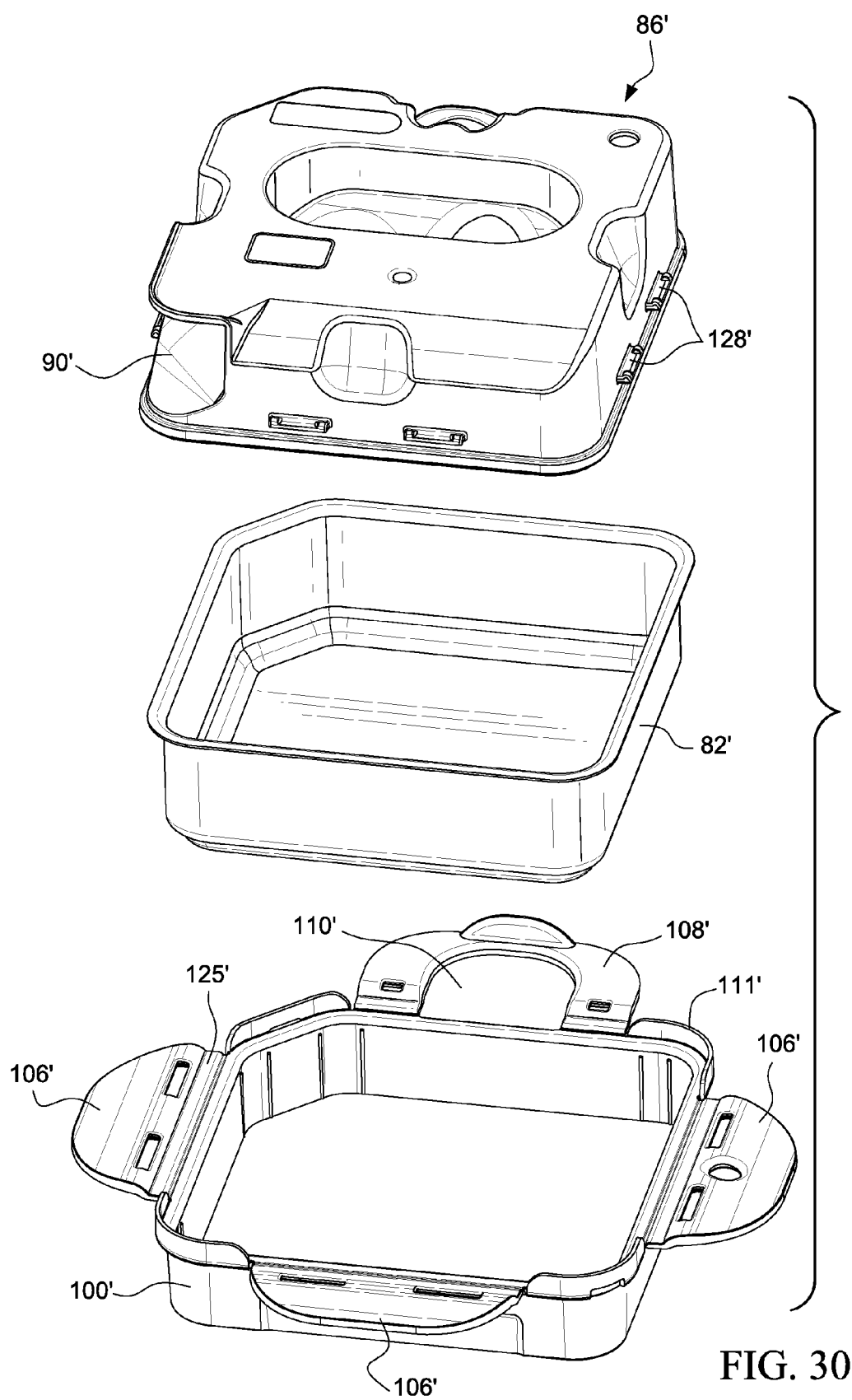
Figure 31:
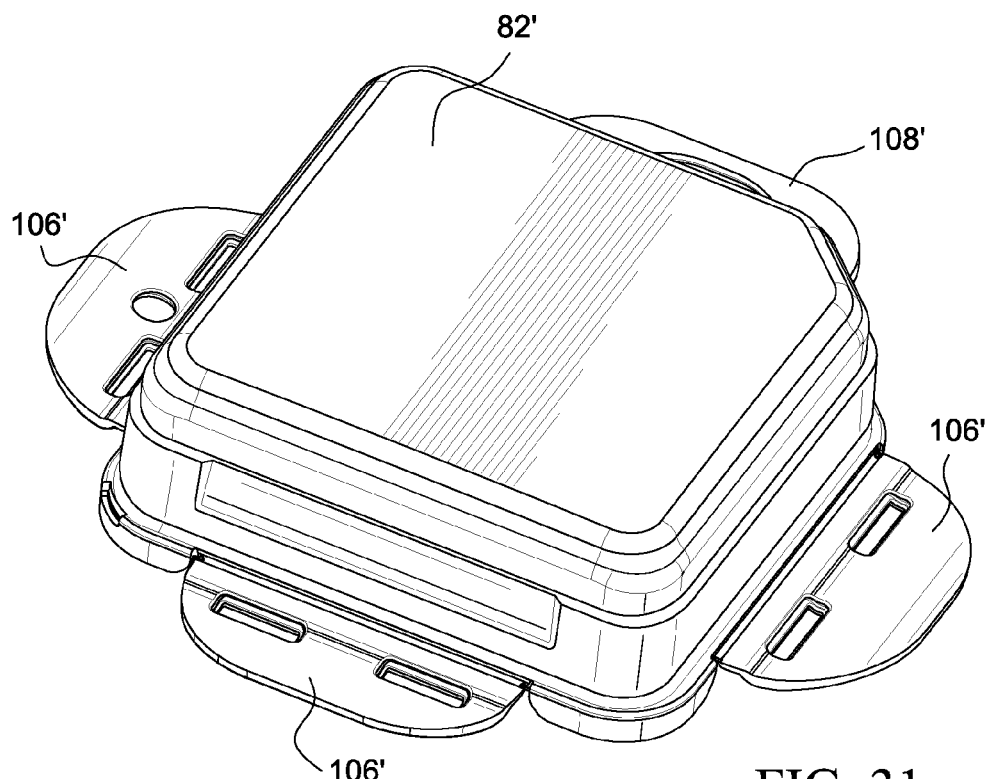
Figure 32:
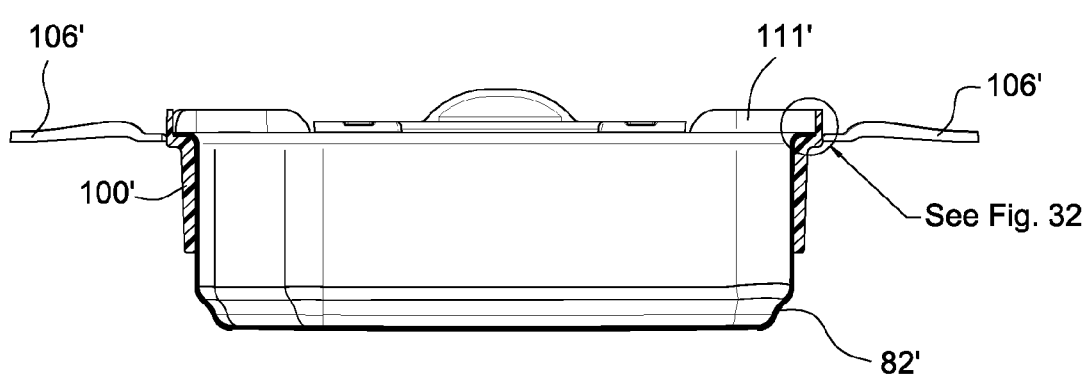

Referring to FIG. 28, a humidifier tub according to another sample embodiment and that is configured to be disposable is illustrated. The humidifier tub 14 may comprise a tub base 82 and a tub lid 86 having a channel 90. The tub lid 86 may be the same as the tub lid of the cleanable humidifier tub discussed with respect to FIGS. 7-25. The tub lid 86 may be secured to the tub base 82 by, for example, welding, adhesive, and/or one or more clips.

The disposable tub base 82 may be formed of, for example, a metal, such as aluminium. It should also be appreciated that the disposable tub base 82 may be formed of other metals or alloys, or from a plastic material.

Humidifier Tub—Seal

Figure 26:
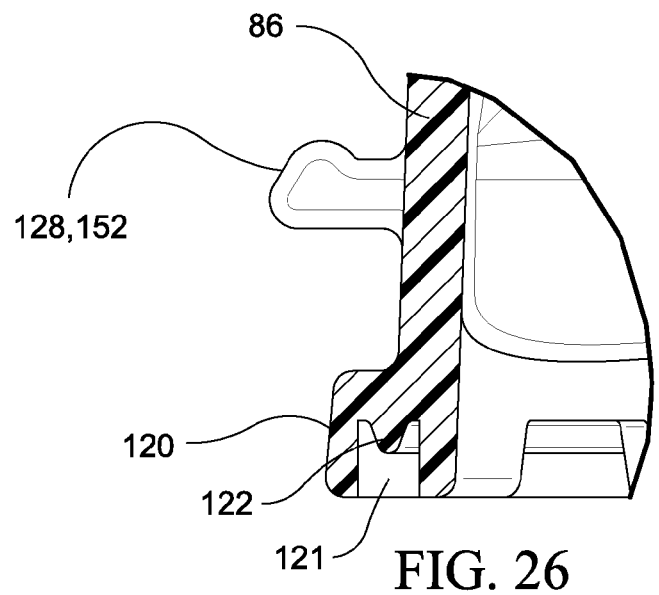
FIG. 26 schematically depicts a rim of the tub lid.
Figure 27:
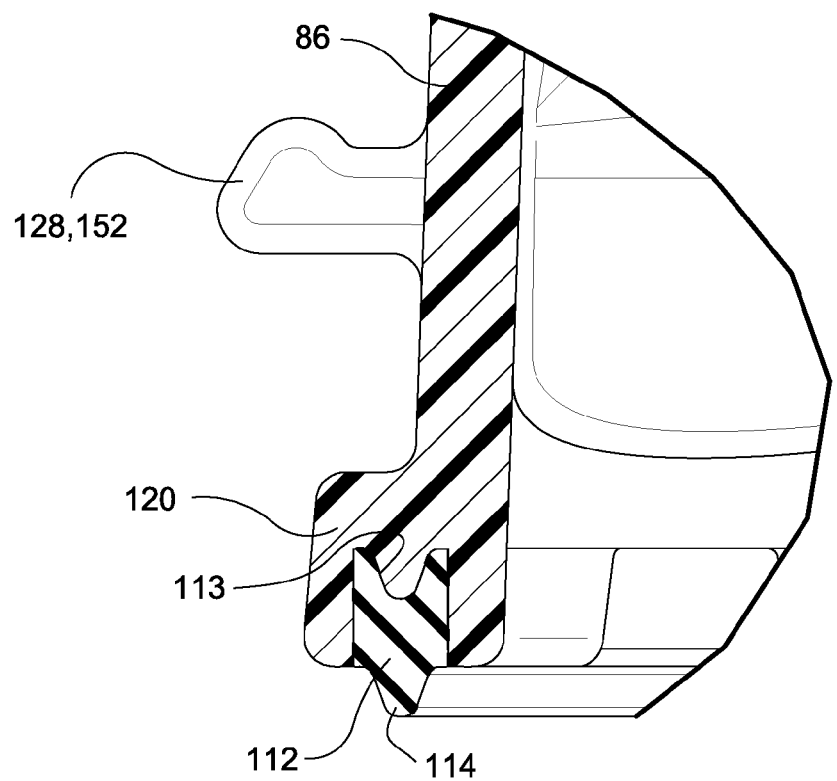
FIG. 27 schematically depicts the rim of the tub lid of FIG. 23 including a seal.
Figure 33:
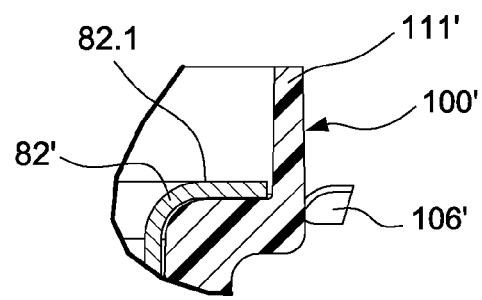
Figure 34:
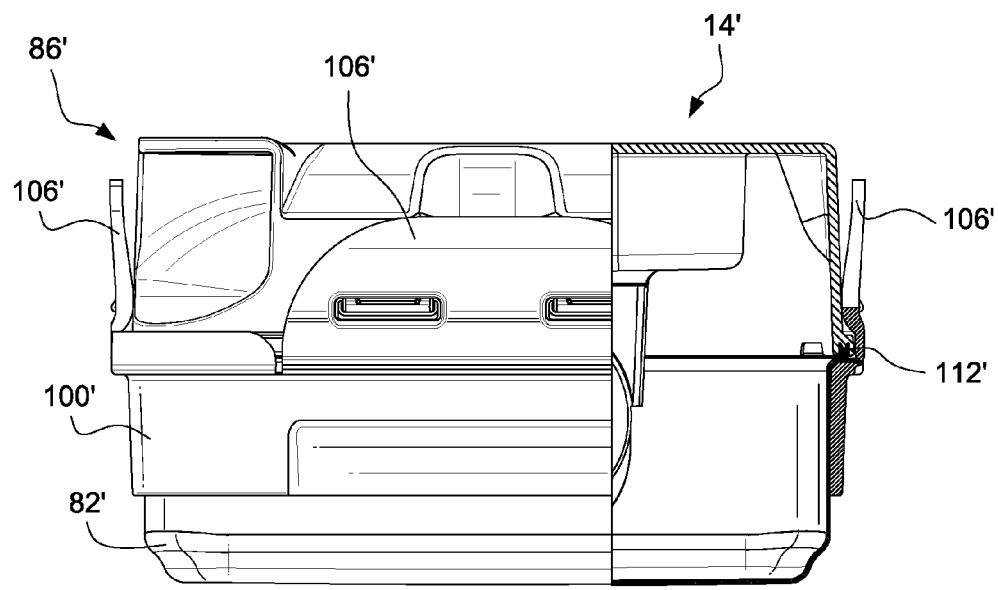
Figure 35:
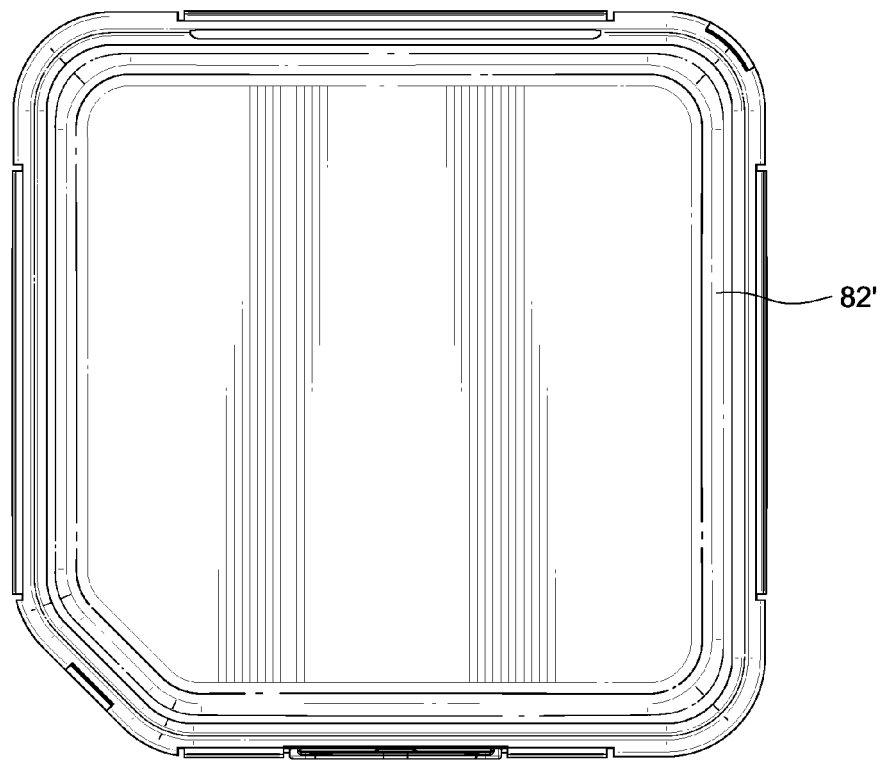
Figure 36:
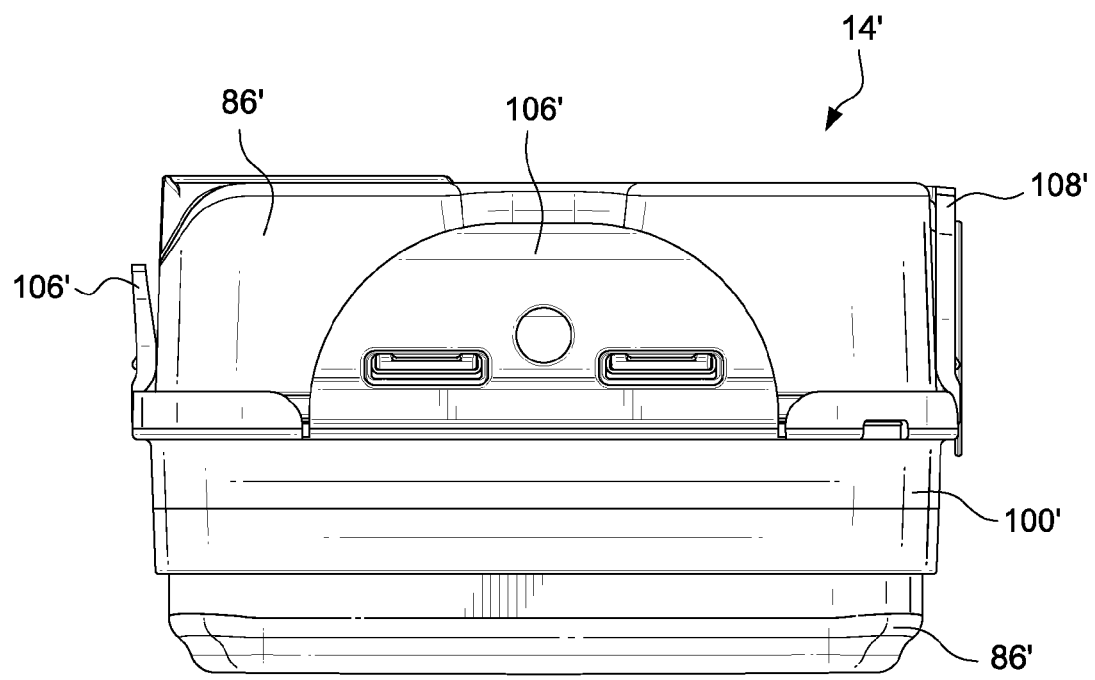
Figure 37:
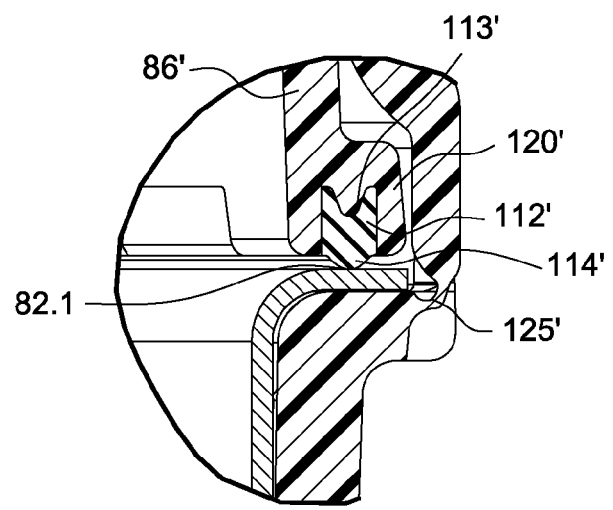

Referring to FIGS. 26 and 27, a seal 112 may be provided on the rim 120 of the tub lid 86. The rim 120 includes a recess, or receptacle, 121 extending around the periphery of the tub lid 86 to receive the seal 112. The recess 121 includes a projection 122 that is configured to be received in a recess 113 of the seal 112. The seal 112 includes a sealing projection, or sealing edge, 114 that is configured to be deformed when the tub lid 86 and the tub base 82 are connected together, for example when the clips 106, 108 of the tub base 82 are connected to the projections 128, 152 of the tub lid 86, or when the tub lid 86 is adhered or welded to the tub base 82. As seen in FIGS. 33 and 37, the base 82' includes a surface 82.1 that engages the projection or edge 114'. The deformation of the sealing projection, or edge, 114 creates a watertight seal between the tub base 82 and the tub lid 86. The projection 122 of the receptacle 121 of the rim 120 of the tub lid 86 directs a force to the sealing projection 114 when the tub base 82 and tub lid 86 are connected to facilitate deformation of the sealing projection 114. It should be appreciated that the tub lid 86 and the seal 112 may be formed of the same material, for example silicone or Thermoplastic elastomer (TPE), and the tub lid 86 and the seal 112 may be integrally formed in one piece. It should also be appreciated that the seal 112 may be formed of, for example, silicone or TPE, and molded on to the tub lid 86.

The humidifier 14 does not include any seals that are provided under the water supply of the tub base 82. The humidifier lid 18 comprises the seal 19 to allow for pressurizing of the humidifier chamber 16 with the flow provided by the flow generator 12 to reduce the pressure on the tub joints, including the disposable tub and the reusable, cleanable tub, thus reducing leaks. Pressurizing the humidifier chamber also reduces tolerances for insertion of the water tub with respect to seals on the inlet of the humidifier and the outlet tube of the humidifier 14.

The seal for the cleanable and reusable tub and the seal for the disposable tub may be formed of different materials and/or different colours. For example, the seal 112 of the cleanable and reusable tub may be formed of silicone. The seal 112 of the disposable tub may be formed of, for example, TPE material, such as Dynaflex G6713-0001—Yellow [PMS 107C], manufactured by GLS Thermoplastic Elastomers (yellow colour pigment by PolyOne Corporation). It should be appreciated that the seals for the reusable and cleanable tub and for the disposable tub may be the same material and/or the same colour. It should also be appreciated that the material of the seal 112 may be moulded onto at least a portion of the water level indicator 320, for example on the indicia 304 and/or 311 and/or on the inclined portion 303, to improve the visibility of the water level indicator.

While the invention has been described in connection with what are presently considered to be the most practical and preferred examples, it is to be understood that the invention is not to be limited to the disclosed examples, but on the contrary, is intended to cover various modifications and equivalent arrangements included within the spirit and scope of the technology. Also, the various examples described above may be implemented in conjunction with other embodiments, e.g., an aspect of one example may be combined with an aspect of another example to realize yet other examples. Further, each independent feature or component of any given assembly may constitute an additional example. Furthermore, each individual component of any given assembly, one or more portions of an individual component of any given assembly, and various combinations of components from one or more examples may include one or more ornamental design features. In addition, while the technology has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise," "comprised" and "comprises" where they appear.

It will further be understood that any reference herein to known prior art does not, unless the contrary indication appears, constitute an admission that such prior art is commonly known by those skilled in the art to which the technology relates.

What is claimed is:

1. A tub configured to contain a supply of water and to be coupled to a humidifier, comprising:
   a tub base configured to contain the supply of water;
   a tub lid connected to the tub base, the tub lid including an inlet configured to receive a flow of breathable gas to be humidified;
   an outlet for the humidified flow of breathable gas; and
   a non-removable water level indicator suspended from the tub lid and configured to indicate a level of the supply of water in the tub base, the water level indicator comprising an inclined portion configured to direct the flow of breathable gas from the inlet away from the outlet, the water level indicator being substantially aligned with the inlet so as to be visible via the inlet when seen from top view.

2. A tub according to claim 1, wherein the water level indicator further comprises a base portion.

3. A tub according claim 2, wherein the inclined portion extends from the base portion.

4. A tub according to claim 1, wherein the water level indicator is coupled to the inlet.

5. A tub according to claim 1, wherein the water level indicator comprises indicia and/or a marking configured to indicate at least a maximum water fill level in the tub base.

6. A tub according to claim 5, wherein the indicia and/or marking is provided on the inclined portion.

7. A tub according to claim 6, wherein the indicia and/or marking includes wording that is oriented vertically so that the wording is progressively covered as the tub base is filled with water.

8. At tub according to claim 7, wherein the indicia and/or marking includes a vertically oriented line adjacent the wording and including an arrow at its top end, oriented towards a filling direction.

9. A tub according to claim 1, wherein the tub lid comprises a channel configured to receive the flow of breathable gas and direct the flow of breathable gas to the inlet, the channel comprising a channel inlet and a channel outlet.

10. A tub according to claim 9, wherein the tub lid comprises a cover portion that covers the channel from the channel inlet to the channel outlet.

11. A tub according to claim 9, wherein the channel is angled upward from the channel inlet to the channel outlet.

12. A tub according to claim 9, wherein the channel outlet is provided in a sump region of the tub lid.

13. A tub according to claim 12, wherein the inlet is provided in the sump region below the channel outlet.

14. A tub according to claim 13, wherein the inlet is provided at a bottom of the sump region and is configured to direct water poured into the sump region into the tub base.

15. A tub according to claim 13, wherein the base portion of the water level indicator is connected to the sump region of the tub lid.

16. A tub according to claim 15, wherein the base portion extends at least partially around the inlet.

17. A tub according to claim 16, wherein the base portion extends half way around the inlet.

18. A tub according to claim 15, wherein the base portion is angled with respect to a vertical axis of the inlet about 1°-10°.

19. A tub according to claim 18, wherein the base portion is angled about 5°.

20. A tub according to claim 1, wherein the water level indicator is integrally formed with the tub lid.

21. A tub according to claim 1, wherein the tub lid comprises a wall extending from a region adjacent the inlet in a direction away from the outlet to direct the flow of breathable gas away from the outlet.

22. A tub according to claim 1, wherein the inclined portion is angled with respect to a bottom plane of the tub lid at just over 90° to just under 180°.

23. A tub according to claim 22, wherein the inclined portion is angled about 125°.

24. A tub according to claim 1, wherein the outlet is angled downwardly at about 25°-35°.

25. A tub according to claim 24, wherein the outlet is angled downwardly about 29.5°.

26. A tub according to claim 1, wherein a top of the outlet is displaced from a top of the lid by about 1 mm-10 mm.

27. A tub according to claim 26, wherein the top of the outlet is displaced about 5.6 mm.

28. A tub according to claim 1, wherein the tub base is formed of metal.

29. A tub according to claim 28, wherein the tub base is formed of stainless steel.

30. A tub according to claim 28, wherein the tub base is formed of aluminum.

31. A tub according to claim 1, wherein the tub lid is formed of plastic.

32. A tub according to claim 31, wherein the tub lid is formed of polycarbonate.

33. A tub according to claim 31, wherein the tub base is transparent.

34. A tub according to claim 31, wherein the tub lid is formed of acrylonitrile butadiene styrene (ABS).

35. A tub according to claim 1, wherein the tub lid is releasably attached to the tub base.

36. A tub according to claim 35, further comprising a latching plate for releasably attaching the tub lid to the tub base.

37. A tub according to claim 36, wherein the latching plate comprises a plurality of clips configured to releasably engage the tub lid.

38. A tub according to claim 37, wherein the plurality of clips are connected to the latching plate by living hinges.

39. A tub according to claim 36, wherein the latching plate comprises a rim configured to engage a rim of the tub base when the latching plate and tub base are connected.

40. A tub according to claim 39, wherein the latching plate comprises a plurality of corner flanges configured to align with a plurality of corners of the tub lid.

41. A tub according to claim 36, wherein the tub base and latching plate are connected by a friction fit.

42. A tub according to claim 36, wherein the latching plate is formed of polypropylene.

43. A tub according to claim 1, wherein the tub lid is connected to the tub base by welding or adhesive.

44. A tub according to claim 1, further comprising:
a seal provided between the tub base and the tub lid.

45. A tub according to claim 44, wherein the seal is provided in a recess of a rim of the tub lid.

46. A tub according to claim 45, wherein the recess of the rim comprises a projection received in a recess in the seal, and the seal comprises a sealing edge that is deformed by the projection upon connection of the tub lid to the tub base.

47. A tub according to claim 44, wherein the seal is formed of thermoplastic elastomer (TPE) or silicone.

48. A tub according to claim 44, wherein the seal is a different colour than the tub lid.

49. A tub according to claim 48, further comprising thermoplastic elastomer (TPE) or silicone the same colour as the seal moulded onto at least a portion of the water level indicator.

50. A tub according to claim 49, wherein the TPE or silicone is moulded onto the inclined portion.

51. A tub according to claim 49, wherein the TPE or silicone is moulded onto indicia and/or a marking on the water level indicator.

52. A humidifier for humidifying a flow of breathable gas to be delivered to a patient, the humidifier comprising:
a chamber configured to receive the flow of breathable gas;
a humidifier lid provided on the chamber and being movable between an open position and a closed position;
a humidifier seal provided on the humidifier lid, the humidifier seal being configured to seal the chamber such that the flow of breathable gas pressurizes the chamber; and
a tub according to claim 1 configured to be inserted into the chamber.

53. A humidifier according to claim 52, wherein the humidifier lid is hinged to the chamber.

54. A humidifier according to claim 52, further comprising an aperture in the chamber and a light, configured to shine through the aperture.

55. A humidifier according to claim 54, further comprising a transparent cover over the aperture.

56. A humidifier according to claim 55, wherein the transparent cover is coloured.

57. A humidifier according to claim 52, wherein the humidifier lid comprises a window and the seal comprises an aperture that surrounds the window.

58. A humidifier according to claim 52, wherein the chamber comprises a cradle.

59. A humidifier according to claim 58, wherein the cradle comprises an inlet configured to receive the flow of breathable gas.

60. A humidifier according to claim 58, wherein the cradle comprises an outlet for the humidified flow of breathable gas.

61. A humidifier according to claim 60, wherein the outlet of the tub lid is configured to deliver the humidified flow of breathable gas to the outlet of the cradle.

62. A respiratory apparatus for delivering a flow of breathable gas to a patient, comprising:
a flow generator configured to generate the flow of breathable gas; and
a humidifier according to claim 52, wherein the humidifier is configured to be connected to the flow generator.

63. A water level indicator for a humidifier tub according to claim 1, wherein a shape of the water level indicator as projected in top view substantially matches a shape of the inlet.

64. A water level indicator for a humidifier tub according to claim 1, wherein the water level indicator has a maximum fill indicator that is visible via the inlet when seen from top view.

65. A tub configured to contain a supply of water and to be coupled to a humidifier, comprising:
a tub base configured to contain the supply of water;
a tub lid connected to the tub base, the tub lid including an inlet configured to receive a flow of breathable gas to be humidified;
an outlet for the humidified flow of breathable gas; and
a non-removable water level indicator suspended from the tub lid and configured to indicate a level of the supply of water in the tub base, wherein the water level indicator is visible through the inlet.

66. A tub according to claim 65, wherein the water level indicator comprises an inclined portion.

67. A water level indicator for a humidifier tub comprising
a base portion configured to be non-removably suspended from a lid of the humidifier tub and having an inclined portion extending therefrom,
the inclined portion configured to direct a flow of breathable gas from a tub inlet away from a tub outlet,
wherein the inclined portion is visible through the tub inlet to provide an indication of a level of water present in the humidifier tub.

68. A water level indicator for a humidifier tub according to claim 67, wherein a shape of the water level indicator as projected in top view substantially matches a shape of the inlet.

* * * * *